(12) United States Patent
Chance

(10) Patent No.: US 7,840,257 B2
(45) Date of Patent: Nov. 23, 2010

(54) EXAMINATION OF BIOLOGICAL TISSUE USING NON-CONTACT OPTICAL PROBES

(75) Inventor: Britton Chance, Marathon, FL (US)

(73) Assignee: Non Invasive Technology, Inc., Philadelphia, PA (US)

( * ) Notice: Subject to any disclaimer, the term of this patent is extended or adjusted under 35 U.S.C. 154(b) by 1921 days.

(21) Appl. No.: 10/752,440

(22) Filed: Jan. 5, 2004

(65) Prior Publication Data

US 2004/0215082 A1 Oct. 28, 2004

Related U.S. Application Data

(63) Continuation-in-part of application No. 10/618,579, filed on Jul. 10, 2003, now abandoned.

(60) Provisional application No. 60/438,229, filed on Jan. 4, 2003.

(51) Int. Cl.
*A61B 6/00* (2006.01)

(52) U.S. Cl. ........................ 600/473; 600/407; 600/476; 600/477

(58) Field of Classification Search ................ 600/407, 600/477, 473, 476
See application file for complete search history.

(56) References Cited

U.S. PATENT DOCUMENTS

| | | | | |
|---|---|---|---|---|
| 4,321,930 A | * | 3/1982 | Jobsis et al. | 600/344 |
| 5,198,977 A | * | 3/1993 | Salb | 382/128 |
| 5,596,987 A | * | 1/1997 | Chance | 600/310 |
| 5,987,351 A | * | 11/1999 | Chance | 600/473 |
| 5,995,856 A | * | 11/1999 | Mannheimer et al. | 600/322 |
| 6,201,989 B1 | * | 3/2001 | Whitehead et al. | 600/476 |
| 6,230,046 B1 | * | 5/2001 | Crane et al. | 600/476 |
| 6,240,309 B1 | * | 5/2001 | Yamashita et al. | 600/407 |
| 2002/0099295 A1 | * | 7/2002 | Gil et al. | 600/476 |
| 2003/0012253 A1 | * | 1/2003 | Pavlidis | 374/45 |
| 2005/0154290 A1 | * | 7/2005 | Langleben | 600/410 |

* cited by examiner

*Primary Examiner*—Brian Casler
*Assistant Examiner*—James Kish
(74) *Attorney, Agent, or Firm*—Ivan David Zitkovsky

(57) ABSTRACT

An optical system for examination of biological tissue includes a light source, a light detector, optics and electronics. The light source generates a light beam to be transmitted to the biological tissue spaced apart from the source. The light detector is located away (i.e., in a non-contact position) from the examined biological tissue and is constructed to detect light that has migrated in the examined biological tissue. The electronics controls the light source and the light detector, and a system separates the reflected photons (e.g., directly reflected or scattered from the surface or superficial photons, i.e., "noise" photons) from the photons that have migrated in the examined biological tissue. This system prevents detection of the "noise" photons by the light detector or, after detection, eliminates the "noise" photons in the detected optical data used for tissue examination.

30 Claims, 19 Drawing Sheets

OXYGENATION
SUBJECT TELLS THE TRUTH

OXYGENATION
SUBJECT TELLS A LIE

EVENT RELATED IMAGE:
15 SECONDS AFTER SUDDEN INSIGHT MINUS
15 SECONDS BEFORE SUDDEN INSIGHT

OXYGENATION

EXAMINATION OF BIOLOGICAL TISSUE USING NON-CONTACT OPTICAL PROBES

This application claims priority from U.S. Provisional Application 60/438,229, filed on Jan. 4, 2003, entitled "Examination of Biological Tissue using Non-Contact Optical Probes," which is incorporated by reference. This application is also continuation-in part of U.S. application Ser. No. 10/618,579, filed on Jul. 10, 2003 now abandoned, entitled "Examination and Imaging of Brain Cognitive Functions," which is incorporated by reference.

The present invention relates to in vivo non-invasive examination or imaging of biological tissue using non-contact spectroscopic systems.

BACKGROUND OF THE INVENTION

X-ray or γ-ray radiation, optical radiation, ultrasound waves and magnetic field have been used to examine and image biological tissue. X-rays or γ-rays propagate in the tissue on straight, ballistic lines, that is, their scattering is negligible. Thus, imaging is based on evaluation of the absorption levels of different tissue types. For example, in roentgenography the X-ray film contains darker and lighter spots. In more complicated systems, such as computerized tomography (CT), a cross-sectional picture of human organs is created by transmitting X-ray radiation through a section of the human body at different angles and by electronically detecting the variation in X-ray transmission. The detected intensity information is digitally stored in a computer that reconstructs the X-ray absorption of the tissue at a multiplicity of points located in one cross-sectional plane.

Near infra-red radiation (NIR) has been used to study biological tissue non-invasively, including oxygen metabolism in the brain, finger, or ear lobe, for example. The use of visible, NIR and infra-red (IR) radiation for medical imaging may have several advantages: In the NIR or IR range the contrast factor between a tumor and a tissue is much larger than in the X-ray range. In addition, the visible to IR radiation is preferred over the X-ray radiation since it is non-ionizing and thus, potentially causes fewer side effects. However, the visible or IR radiation is strongly scattered and absorbed in biological tissue, and the migration path cannot be approximated by a straight line, making inapplicable certain aspects of cross-sectional imaging techniques.

Optical spectroscopy has been used to monitor and image tissue blood oxygenation and volume by measuring absorption of oxyhemoglobin and deoxyhemoglobin in the near infrared (NIR) wavelength region. Below 700 nm, light is strongly absorbed by hemoglobin, and above 900 nm, it is strongly absorbed by water. By making differential measurements at either side of the isosbestic point of oxyhemoglobin and deoxyhemoglobin absorbance (near 800 nm), it is possible to quantify the blood oxygenation and volume levels. Typically, these measurements are made at 750 nm and 830 nm.

NIR spectrometry adapted to the principles of computerized tomography has been used for in vivo imaging. This technique utilizes NIR radiation in an analogous way to the use of X-ray radiation in an X-ray CT. The X-ray source is replaced by several laser diodes (or other light sources) emitting light in the NIR range. The NIR-CT uses a set of photodetectors that detect the light that had migrated in the imaged tissue. The detected data are manipulated by a computer in a manner similar to the detected X-ray data in an X-ray CT. Different NIR-CT systems have recognized the scattering aspect of the non-ionizing radiation and have modified the X-ray CT algorithms accordingly.

Brain tissue has been particularly studied by many burgeoning technologies, wherein MRI is truly versatile as being capable of imaging hemodynamic and metabolic signals in a unique fashion. PET has similar possibilities of large chemical specificity governed by the combination of lifetimes and radiation from radioactive isotopes. Other methods give highly specialized signals, for example, MEG and EEG that have respectively high and low resolution for neurophysiological signals. Optical tomography is somewhat more quantitative with respect to hemodynamic changes and has latent possibilities for measuring neuronal signals.

Furthermore, the propagation of near infrared light through biological tissue such as the brain and breast has been experimentally studied and theoretically modeled. Accurate theoretical models are based on Monte Carlo representations of the diffusion equation and on analytic expressions that show propagation into the gray matter of the brain in adults and especially in neonates. This propagation of light into cranial tissue has been verified by clinical measurements of the presence of X-ray CT identified cranial hematomas at depths of about 3-4 cm. Detection of the oxygenation state and amount of hemoglobin has been the goal of tissue oximetry and quantitative results are obtained by time and frequency domain devices. However, single volume determination of optical parameters of a highly heterogeneous system such as the human brain may give only a fraction of the signal of a localized focal activation already shown to be highly localized by fMRI (functional Magnetic Resonance Imaging).

The optical systems are relatively simple, safe, portable and affordable as required by today's health care industry. There are several optical examination and imaging devices that have been used for imaging functional activity of adult, full-term and pre-term neonate brain. These optical examination and imaging systems are described in U.S. Pat. Nos. 5,353,799; 5,853,370; 5,807,263, 5,820,558, which are incorporated by reference. These optical systems do not require subject immobilization (as do MRI and PET), nor do they require multi-subject averaging of data. The images are acquired in less than half a minute and show two dimensional resolution of blood changes to better than a centimeter. In these optical systems, however, light sources and light detectors are mounted directly next to the examined tissue or the light is coupled to the tissue using light guides (e.g., optical fibers). In these optical systems, however, the subject has to wear the optical coupler or probe. Furthermore, the optical probe has to provide electrical insulation to prevent electrical shock to the subject.

There is still a need for optical examination and imaging systems for examining various types of biological tissue including the brain or breast tissue.

SUMMARY OF THE INVENTION

The present invention is a method and system for in vivo non-invasive examination or imaging of biological tissue using non-contact spectroscopic systems.

According to one aspect, an optical system for examination of biological tissue includes a light source, a light detector, optics and electronics. The light source generates a light beam to be transmitted to the biological tissue spaced apart from the source. The light detector is located away (i.e., in a non-contact position) from the examined biological tissue and is constructed to detect light that has migrated in the examined biological tissue. The electronics controls the light source and the light detector, and a system separates the reflected photons (e.g., directly reflected or scattered from the surface or superficial photons) from the photons that have migrated in the examined biological tissue. The system prevents detection of the "noise" photons by the light detector or, after detection, eliminates the "noise" photons in the detected optical data used for tissue examination.

The optical system including its electronics may comprise a time-resolved spectroscopic (TRS) system, a phase modulation system (PMS), a phased array system, or a continuous wave (CW) system. In each case, the detector is located away from the examined tissue and there is no optical fiber in contact with the tissue surface. Conventionally, this reduces the light collection efficiency (reduces the effective numerical aperture), which in prior art was considered as a barrier to an effective spectrophotometric system. Thus, the present invention "discarded" the conventional concept.

According to another aspect, an optical system for examination of brain tissue of a subject undergoing a security check includes a light source, a light detector, optics and electronics. The light source generates a light beam to be transmitted to the head of the subject spaced apart from the source. The light detector is located away from the head and is constructed to detect light that has migrated in the biological tissue being examined. The electronics controls the light source and the light detector, and a system separates the reflected photons from the photons that have migrated in the examined biological tissue to prevent detection of the reflected photons by the light detector or eliminate after detection the reflected photons in the detected optical data used for tissue examination.

Preferred embodiments of these aspects include one or more of the following features: The optical system includes a lens associated with the light detector (e.g., a fresnel lens for a CW system). The light detector includes an intensified charge coupled device (ICCD). The light source is associated with a scanning system for scanning the emitted light beam over a tissue area.

The electronics includes a TRS system, a phase modulation system (PMS), a phased array system, or a CW system. The system evaluates the detected light to determine a brain function of the subject. The system evaluates the detected light to determine truthfulness of statements by the subject.

The system also provides brain stimulation. The brain stimulation includes providing visual stimulation. The brain stimulation includes stimulating cognitive function of the brain. The brain stimulation includes stimulating memories stored in the brain. The brain stimulation includes providing auditory stimulation.

A system and method for examining a brain function of a subject introduces optical radiation from a light source into the brain of a subject and detects radiation that has migrated in a brain region from the light source to a detector. The system also provides brain stimulation and evaluates the detected radiation to determine a brain function or malevolence of the subject.

Furthermore, the described systems can be used as "deceit measure detectors" that provide strong signal at the signature voxel when the subject is lying and provide weak signal at the signature voxel when the subject is telling the truth.

BRIEF DESCRIPTION OF THE DRAWINGS

FIGS. 4, 4A, 4B, and 4C show schematically a TRS system used for non-contact optical examination or imaging, wherein FIG. 4 is a schematic block diagram of the TRS system using a single boxcar integrator, FIG. 4A is a schematic block diagram of a related TRS system using multiple boxcar integrators, FIG. 4B is a timing diagram for the TRS system of FIG. 4A, and FIG. 4C shows a typical time resolved spectrum collected by the TRS system of FIG. 4A.

DESCRIPTION OF PREFERRED
EMBODIMENTS

Figure 1:
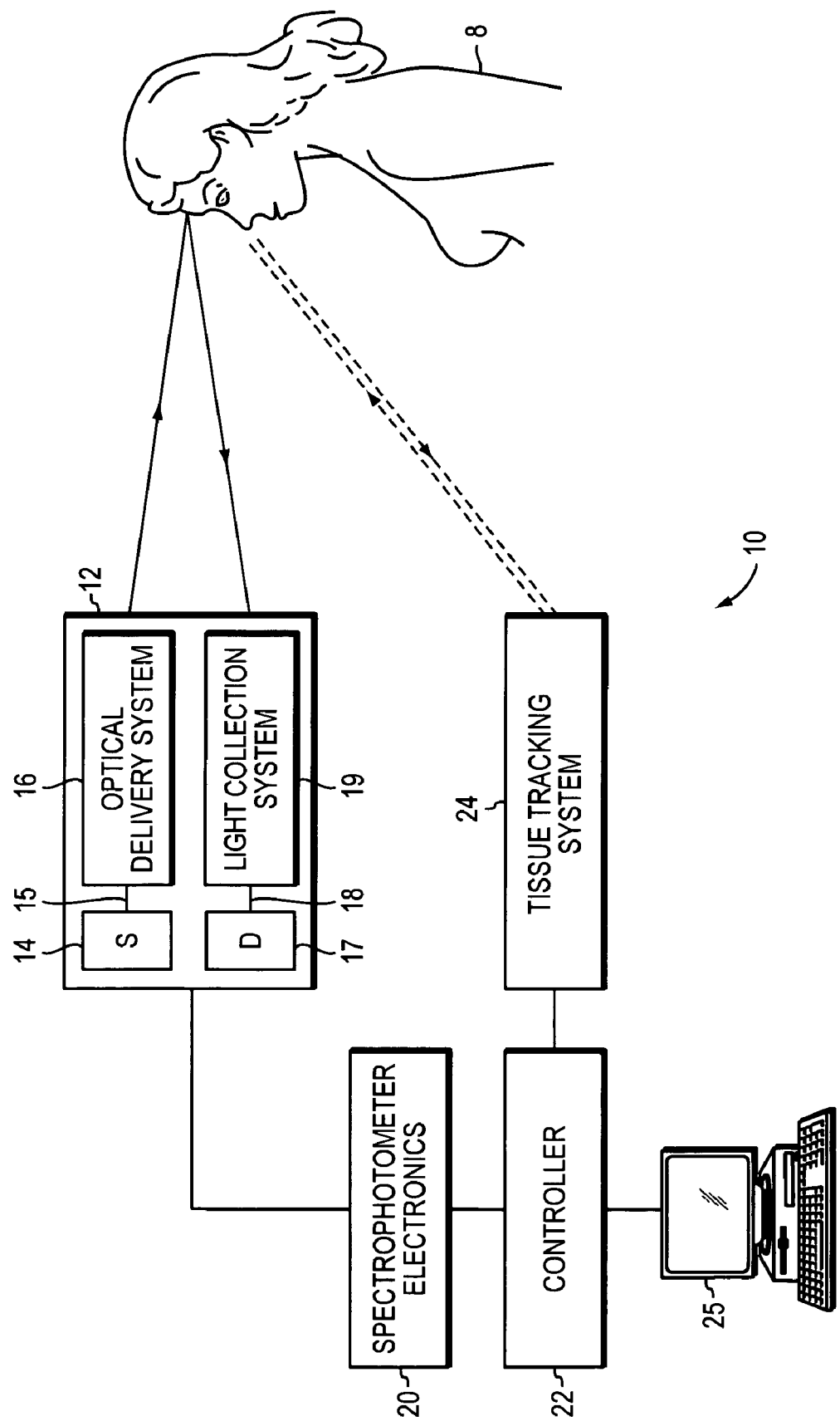
FIG. 1 shows schematically a non-contact optical examination or imaging system having an optical probe, including a light source and a light detector, remotely located from the examined biological tissue.

FIG. 1 shows schematically a non-contact optical system 10 including a non-contact optical probe 12, spectrophotometer electronics 20, a system controller 22, a tissue tracking system 24 and a computer 25. Spectrophotometer electronics 20 controls optical probe 12, including light emission from a light source 14, light delivery or scanning by an optical delivery system 16, light collection and receiving by a light collection system 19 and the corresponding detection by a light detector 17. Light source 14 emits a light beam of a selected wavelength focused and/or scanned over the examined tissue surface by delivery system 16. Light detector 17 receives light from a light collection system 19, which collects light emanating from the tissue surface. A controller 22 controls the entire operation of the spectrophotometer (including electronics 20 and optical probe 12) and controls operation of a tissue tracking system 24.

Tissue tracking system 24 is optional and operates together with non-contact optical probe 12 by "locating" a selected tissue region, and providing focusing data to the optics of probe 12. The simplest embodiment of tissue tracking system 24 includes an automatic focusing system used in optical cameras or video recorders. Alternatively, tissue tracking system 24 provides a picture or another type of optical image of the tissue of interest to computer 25, wherein the operator can select the irradiation region of the examined tissue surface for light delivery system 16, based on an optical image collected by the tissue tracking system. Alternatively, tissue tracking system 24 may include optics and electronics of an optical or video camera (operating in the visible or infra-red range). Tissue tracking system 24 can automatically provide focus and raster information to optical probe 12, accounting for a moving biological tissue of interest during examination and imaging. Even though schematically shown separately, tissue tracking system 24 may be constructed as an integral part of optical probe 12, using even the same light source and detector.

The entire non-contact, remote optical system uses spectrophotometer electronics 20, which may be a CW (continuous wave) spectrophotometer described in PCT application PCT/US95/15666, which is incorporated by reference. Alternatively, the spectrophotometer is a TRS system (time resolved spectroscopic system) as described in PCT applications PCT/US94/03518 or PCT/US94/07984 or U.S. Pat. No. 5,119,815; or U.S. Pat. No. 5,386,827, all of which are incorporated by reference. In another embodiment, the spectrophotometer is a phase modulation system described in U.S. Pat. Nos. 4,972,331; 5,122,974; 5,187,672; 5,553,614; 5,564,417; PCT application PCT/99/03066; PCT application PCT/99/02953; and PCT application PCT/99/03030, all of which are incorporated by reference. In another embodiment, the spectrophotometer is a phased array, phase cancellation system described in PCT application PCT/US93/05868 or an amplitude cancellation system described in PCT application PCT/US95/15694, both of which are incorporated by reference as if filly set forth herein.

Figure 1A:
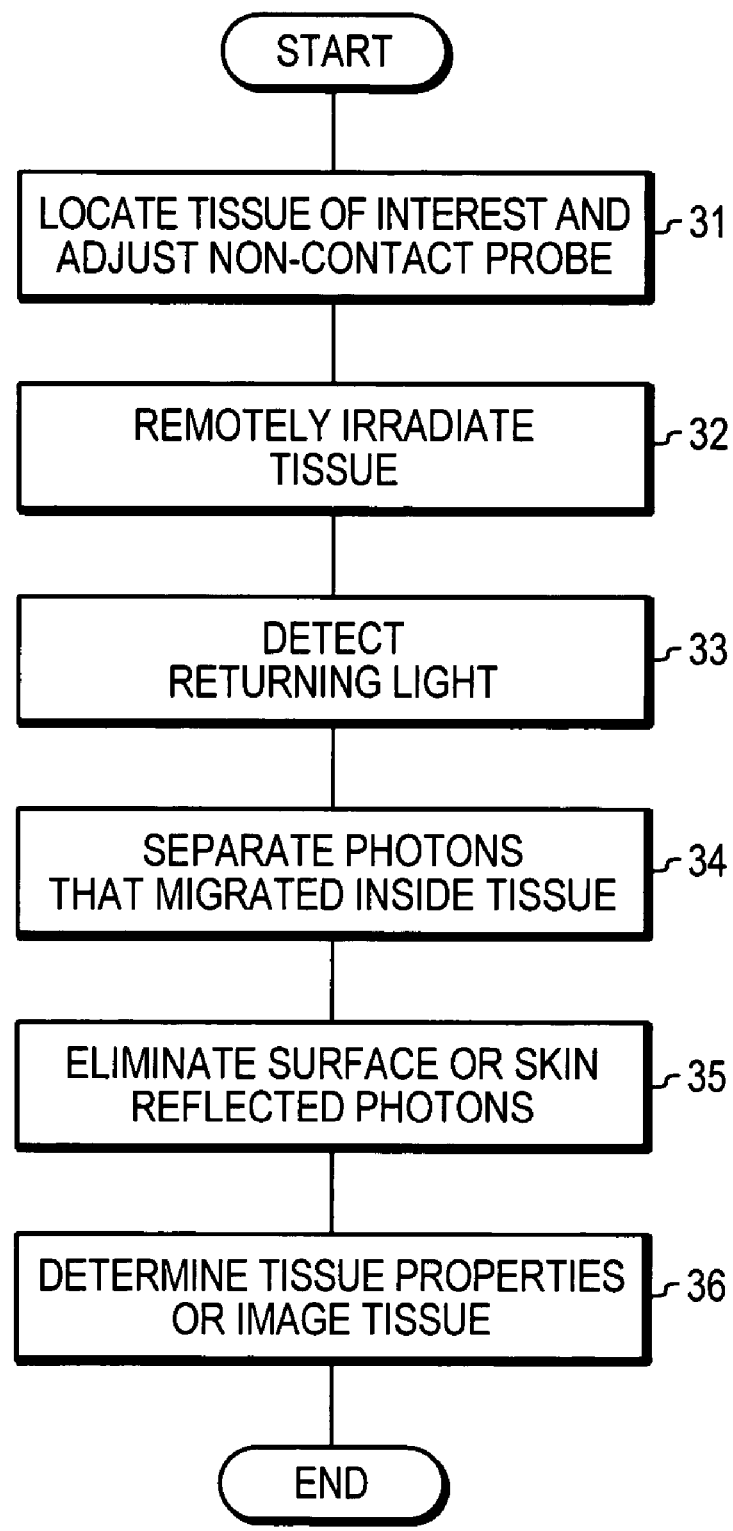
FIG. 1A illustrates schematically an examination and imaging process preformed by the system of FIG. 1.

FIG. 1A illustrates schematically an examination and imaging process preformed by the system of F*ig*. 1. The entire process is controlled by computer 25, which executes all data acquisition and processing algorithms. Initially, tissue tracking system 24 locates a tissue region of interest. The tissue region of interest may be displayed on the monitor of computer 25, and an operator can select the size of the examined region, the raster density and area, the acquisition time and other parameters. Then, tissue tracking system 24 "locks on" the selected tissue area and provides orientation and focusing data to light delivery system 16 and light collection system 19 of non-contact optical probe 12 (step 31).

Light source 14 emits a light beam 15 of a selected wavelength, and optical delivery system 16 scans and/or directs the irradiation light to the selected tissue area (step 32). Light collection system 19 collects the returning light and light detector 17 detects the light provided by light collection system 19, as described below (step 33). In steps 34 and 35, the system separates the "useful" photons that migrated in the examined tissue from the "unwanted" photons returned due to specular reflection or reflection from the skin layers. This separation may be done optically or electronically.

The system acquires optically only the "useful" photons, for example, by using confocal detection, polarized light, or detecting fluorescent radiation excited inside the tissue of interest. For example, light source 14 emits a light beam that is polarized by a polarizer (included in optical delivery system 16), which polarized light beam is scanned over the irradiation location of the examined tissue. Reflected photons maintain polarization, while the useful migrating photons lose polarization. Thus, the system can optically eliminate the reflected light. Alternatively, optical delivery system 16 and light collection system 19 include a pinhole for confocal detection (or pseudo-confocal detection) of photons from a selected depth inside the examined tissue. Alternatively, light source 14 emits a light beam of a wavelength selected to excite fluorescent radiation inside the examined tissue. Light collection system 19 includes a suitable interference filter and thus light detector 17 detects the fluorescent light excited inside the examined tissue.

The system separates electronically or computationally the detected signal to receive only the "useful"photons. As described in connection with FIGS. 4, 4A, 4B and 4C, a time resolved spectroscopic system (TRS) eliminates the reflected photons using proper timing of the gates shown in FIG. 4B. The time resolved spectroscopic system eliminates the reflected photons using proper timing of the gates shown in FIG. 4B.

Figure 1B:
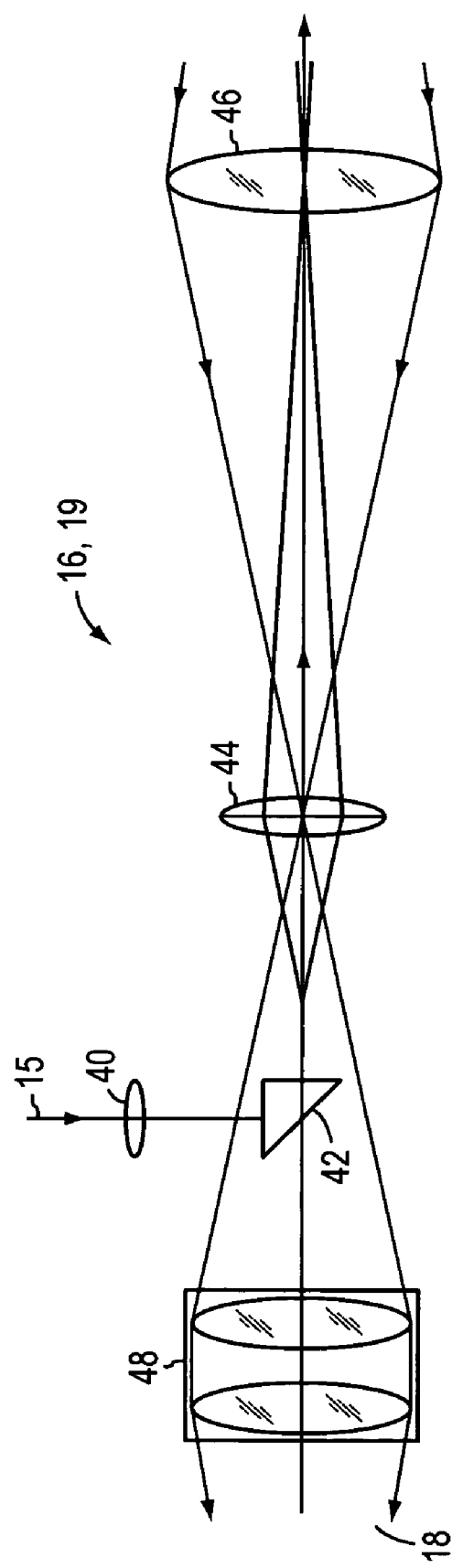
FIG. 1B illustrates schematically an optical delivery and collection system used in the system of FIG. 1.

FIG. 1B illustrates schematically an optical delivery and collection system (a combination of systems 16 and 19) used in the system of FIG. 1. This system is designed for direct imaging or for scanning the image over the detector. The optical delivery and collection system includes a large objective lens 46, a lens 44, and a detector lens system 48. Objective lens 46 forms an intermediate image of the examined tissue 8 and this is transferred to detector 17 by detector lens system 48. The irradiation laser beam 15 is focused by a lens 40 to a small prism 42 (or a mirror). The light scattered directly at the sample surface is blocked by prism 42.

The light collected from the examined tissue 8 by the large objective lens 46 forms an intermediate image in the plane of lens 44. Detector lens system 48 is constructed and arranged to transfer the first image into detector 17, which is preferably a multianode PMT. Detector lens system 48 uses two or more lenses to obtain a higher aperture while maintaining an acceptable image quality.

Referring still to FIG. 1B, the scanning design includes a scan mirror assembly located between prism 42 and lens 44. As described above, objective lens 46 forms an intermediate image of the examined tissue, which is transferred to the detector by detector lens system 48. The input laser beam 15 is provided through lens 40 and prism 42 (or a mirror) and focused on lens 44. Lens 44 is the 'scan lens' that sends the laser at a variable angle through a stationary spot at the center of objective lens 46. A baffle in front of the detector may be used to block light scattered directly at the tissue surface. Photons detected by, for example, an 8×8 PMT detector are recorded into several separate channels and assigned to the different scan positions. This gives a n-dimensional data array for two detector coordinates, two source coordinates, and the time in the time of flight measurement. The system may include also a polarizer and may be adapted for detecting fluorescent light excited in the examined tissue.

Figure 2:
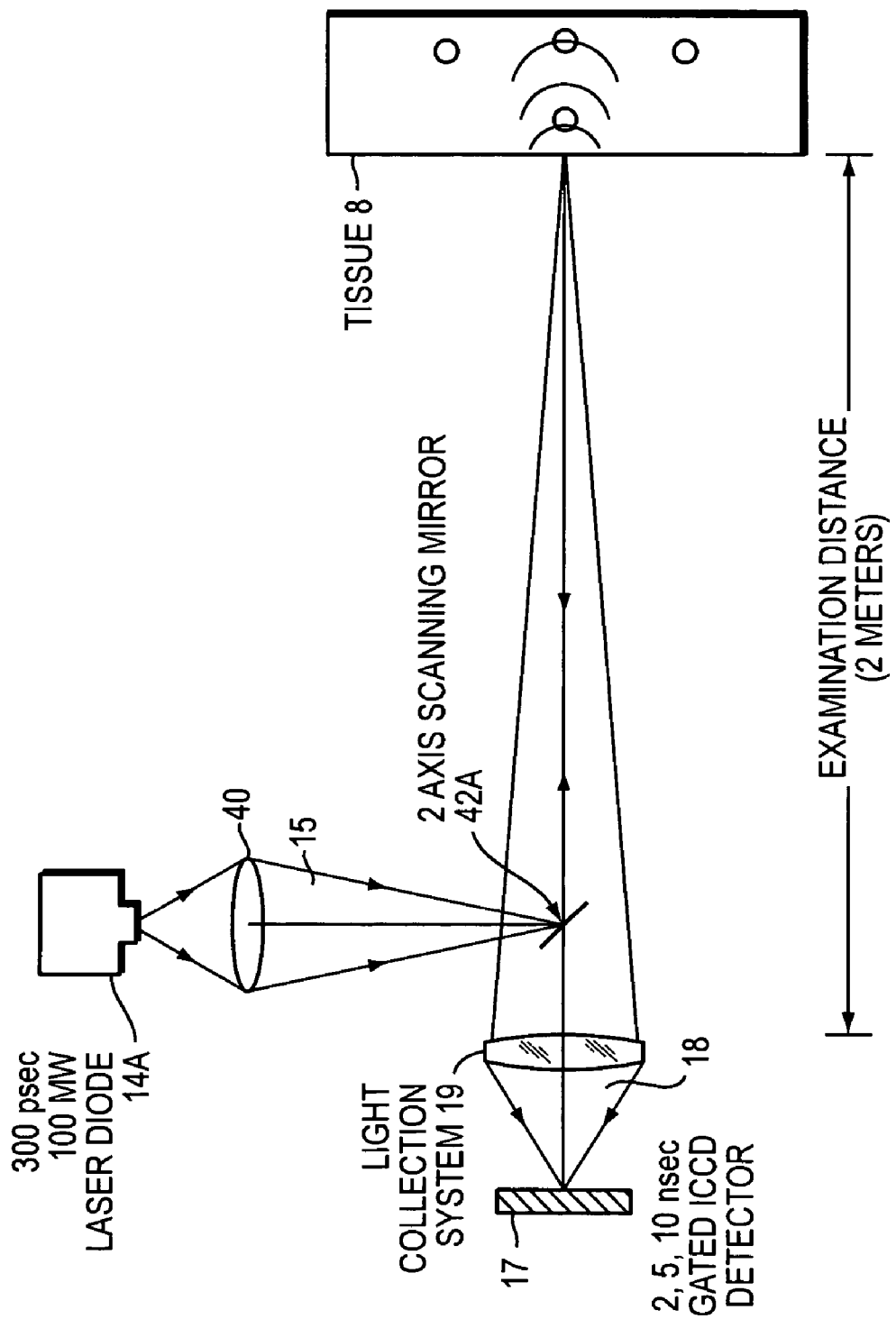
FIG. 2 shows schematically a non-contact optical examination system having a light source and a light detector remotely located from the examined biological tissue.

FIG. 2 shows schematically a non-contact optical system including optical delivery system 16 and light collection system 19. Optical delivery system 16 includes a scanning mirror 42A for scanning a light beam emitted from light source 14A over two dimensions. Specifically, mirror 42A guides the laser beam to tissue 8 by scanning in 2 axes in the flying spot manner. Light collection system 19 is arranged on axis with the scanned beam to receive returning light from tissue 8. Light collection system 19 provides the collected light to light detector 17. Light detector 17 is an intensified charge coupled device (ICCD) that is gated at 2, 5 and 10 nanoseconds.

Importantly, the non-contact optical system irradiates biological tissue with photons of at least one selected wavelength and then detects photons that have migrated in the tissue and exited the tissue (i.e., emergent photons), but separates the "reflected" photons, i.e., photons that were reflected from the tissue surface and thus provide "no tissue property information" since these photons did not migrate within the tissue. This separation may be done using different techniques depending on the spectroscopic system. For example, the TRS system described below uses light pulses of about 2 nanoseconds to distinguish between the reflected photons that reach the detector first and the photons that have migrated in the tissue prior to detection, which photons are delayed several nanoseconds. Other spectrophotometric systems separate the reflected photons from the emergent photons using optical barriers, various properties of light such as polarization, different wavelengths such as excitation and fluorescent wavelength, and other methods.

Figure 2A:
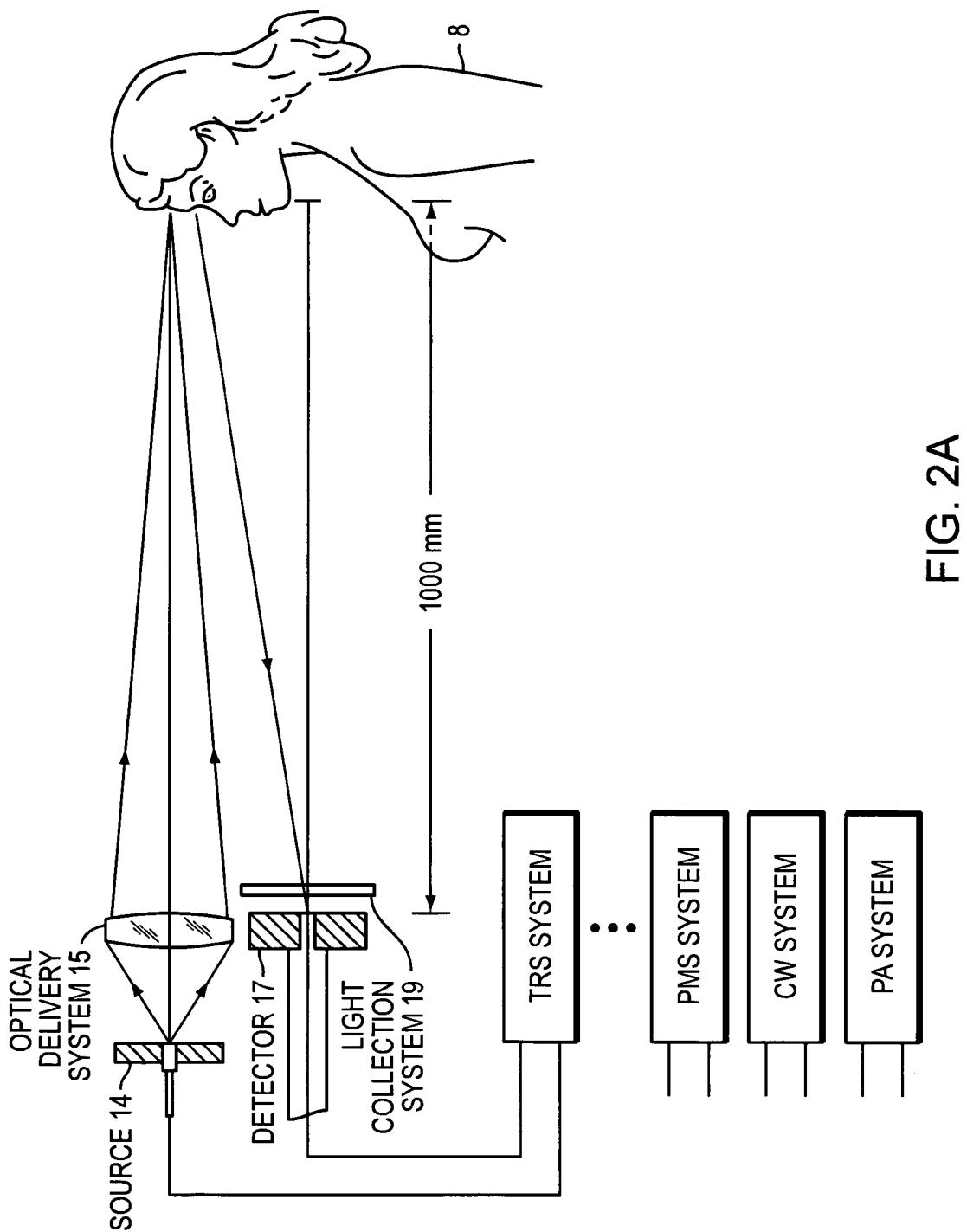
FIG. 2A shows schematically another embodiment of an optical examination system having the light source and the light detector remotely located from the examined biological tissue.

The spectrophotometer of FIG. 2A uses a similar scanning and light collection system. The non-contact optical probe may be connected to a TRS system, a PMS system, a CW system, or a phased array (PA) system. This system may be used for different applications, including medical applications, security applications or malevolence detection, as described below.

Figure 2B:
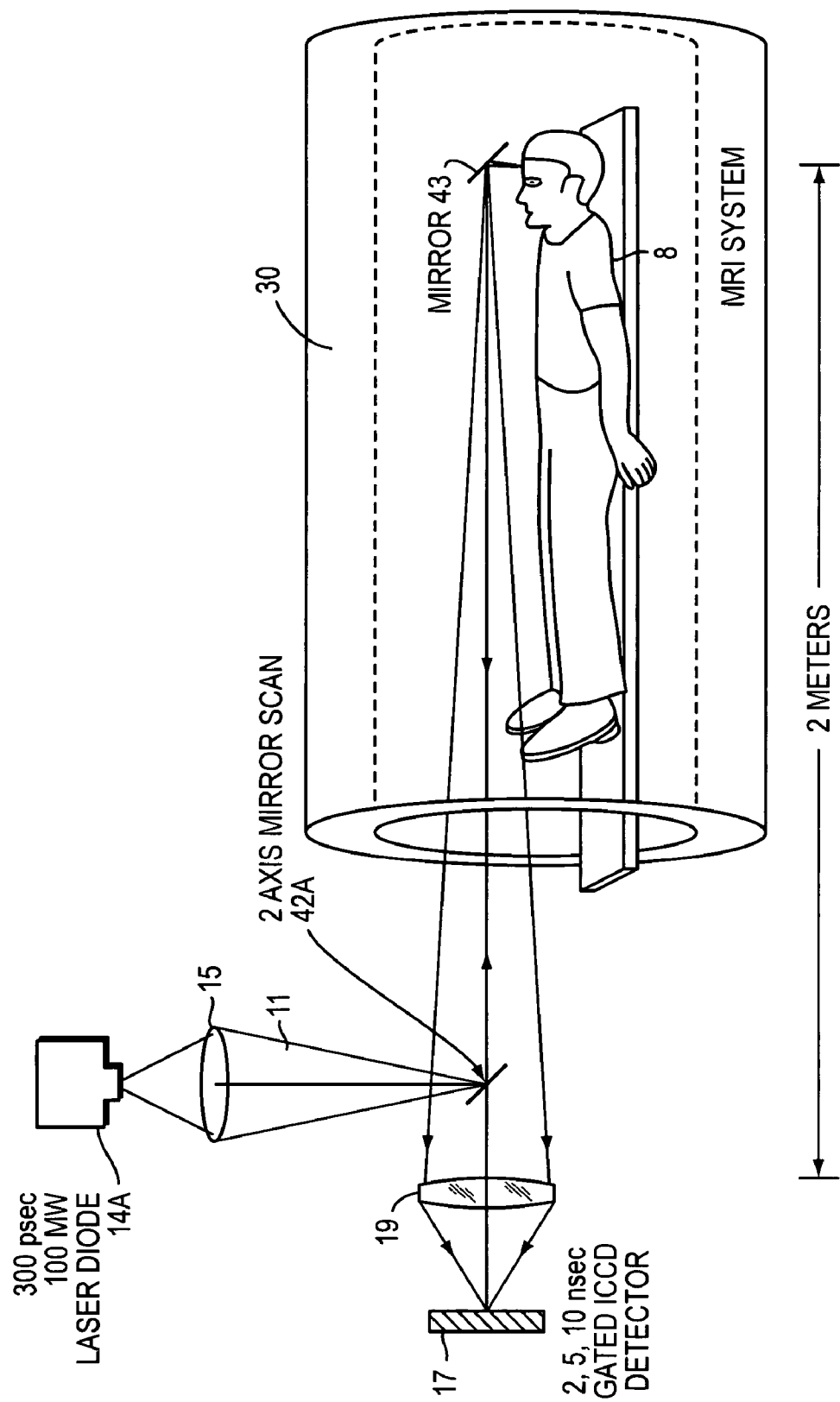
FIG. 2B shows schematically another embodiment of the optical examination system used for examination together with an MRI system.

Referring to FIG. 2B, a non-contact TRS system is designed for use with an MRI magnet used, for example, for MRI or fMRI examination. The TRS system includes light source 14A providing 300 picosec. light pulses and light detector 17, which is an ICCD. Coaxial mirror 42A sends the illumination beam 11 along the axis of lens system 19 and another mirror 43 (also used for observations of the subject) directs photons to and from the forehead of subject 8. Mirrors 42A and 43 may be scanned to scan light over the forehead in the flying spot manner to obtain an image of the human forehead (or any other biological tissue). The NMR coil (not shown) is arranged in a squirrel cage manner so that optical access to the forebrain is possible. A computer collects the data and displays the data corresponding to the remitted photons from the brain as a logarithmic progression, or as a gated output of 2, 5 and 10 nanoseconds, as shown in FIGS. 4C or 5A.

Figure 3:
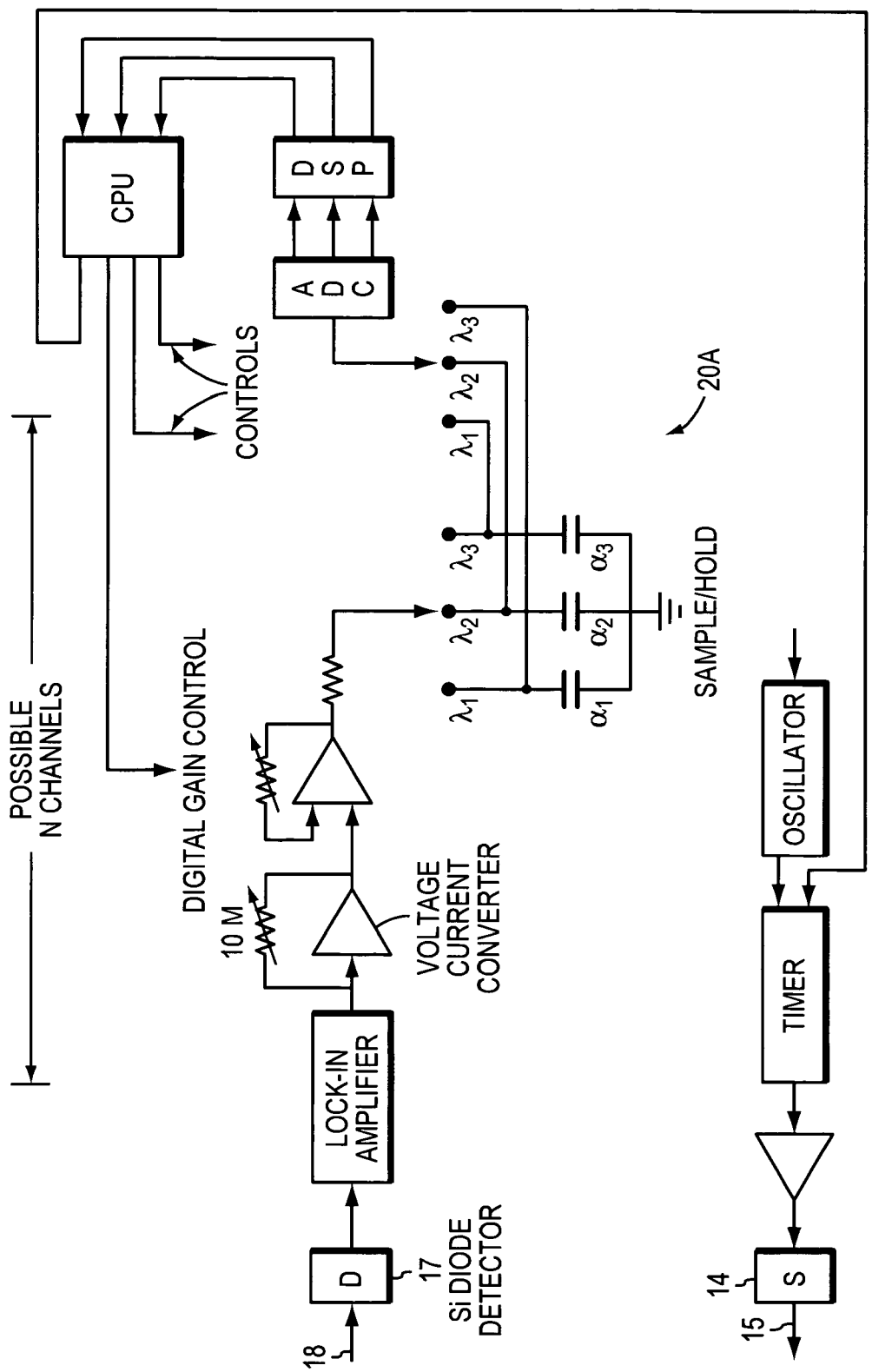
FIGS. 3 and 3A show schematically a CWS system used for non-contact optical examination or imaging.
Figure 3A:
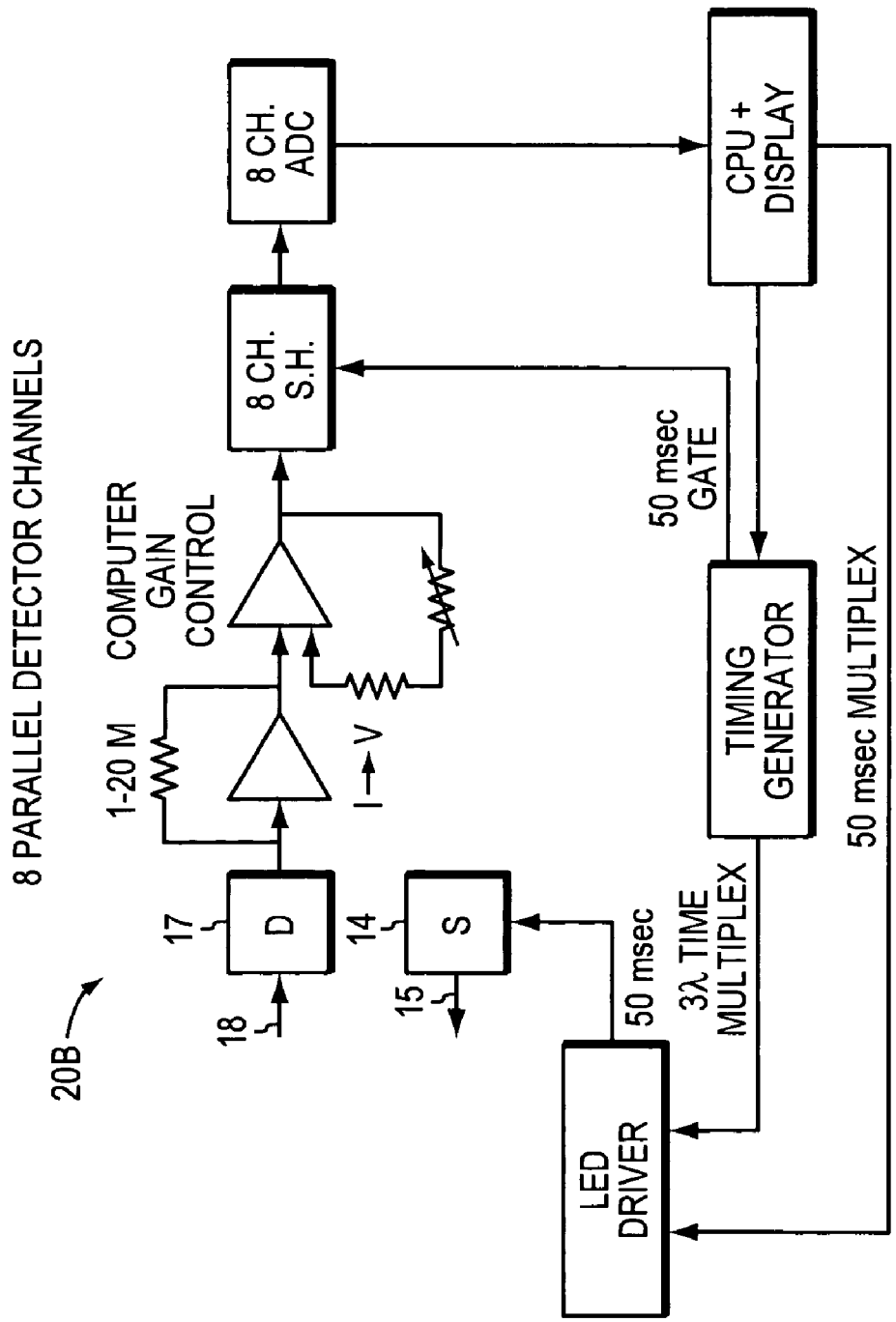

FIGS. 3 and 3A show schematically electronics 20A and 20B of a CWS system used for non-contact optical examination or imaging. FIG. 3 shows schematically a three-wavelength optical module designed for examination and imaging of cognitive functions. The system includes a gain control for calibrating the optical signal in μM, prior to brain examination, as described below. The optical data are provided to a computer in a digital format. FIG. 3A shows schematically another embodiment of a three-wavelength, noncontact optical module. The electronics 20B uses eight parallel channels for receiving optical data. This imager uses a probe having 8-channels, the input to each channel is obtained from one of the eight silicon diode detectors located around a single 3-wavelength LED source. It uses the frequencies in the ISM band to transfer the data from the probe to the remote receiver, where the data acquisition and analysis are done. The synchronization between the transmitter and the receiver is achieved using the Sync pulses, produced by the timing circuitry at the probe and transmitted every cycle.

In the system of FIG. 3A, everything is localized with a mercury battery timer and driver for the two or 3 wavelength LED a mercury battery operated silicon diode CMOS detector and a radio transmitter using an RF frequency encoded system so that all 8 detectors are at a different transmitter frequency. Time multiplex is less complicated i.e., the only timer here is the light source that gives the 2 or 3 wavelengths and then a dark interval, which is used as a synchronizer. This gives the ultimate flexibility and a good measure of non-transmission from source to detector because each detector is recessed with the rubber rim around the edge of the light source.

For example, in order to exactly equalize the outputs from several integrated chip silicon diode detectors, there may be a fifty-dB digitally controlled gain stage. The output in the region of 1-5 V pulses at 5 ms time multiplex pulses are connected to a sample-and-hold circuit in order to obtain an averaged "peak value" over 100 ms. Here, simple reed switches are adequate to give closure during the peak value of the input signals at the three wavelengths as are provided by the computer clock-controlled time-sequenced switches. Instead of taking the output at the time of closure of the input switches, the averaged value is sampled by the ADC program at an interval when the charge on the capacitors has stabilized and an average value of over the preceding twenty (20) closures of the switch is obtained. Thus, ADC sampling can take place at any time except when the signal switches are activated to impart new information to the holding circuit. An 8-bit ADC is quite adequate and digital signal processing (DSP) thereafter is optimal in view of the excellent averaging properties of the sample-and-hold circuit. The back projection algorithm for imaging provides information for each one of the 16 sectors.

Figure 4:
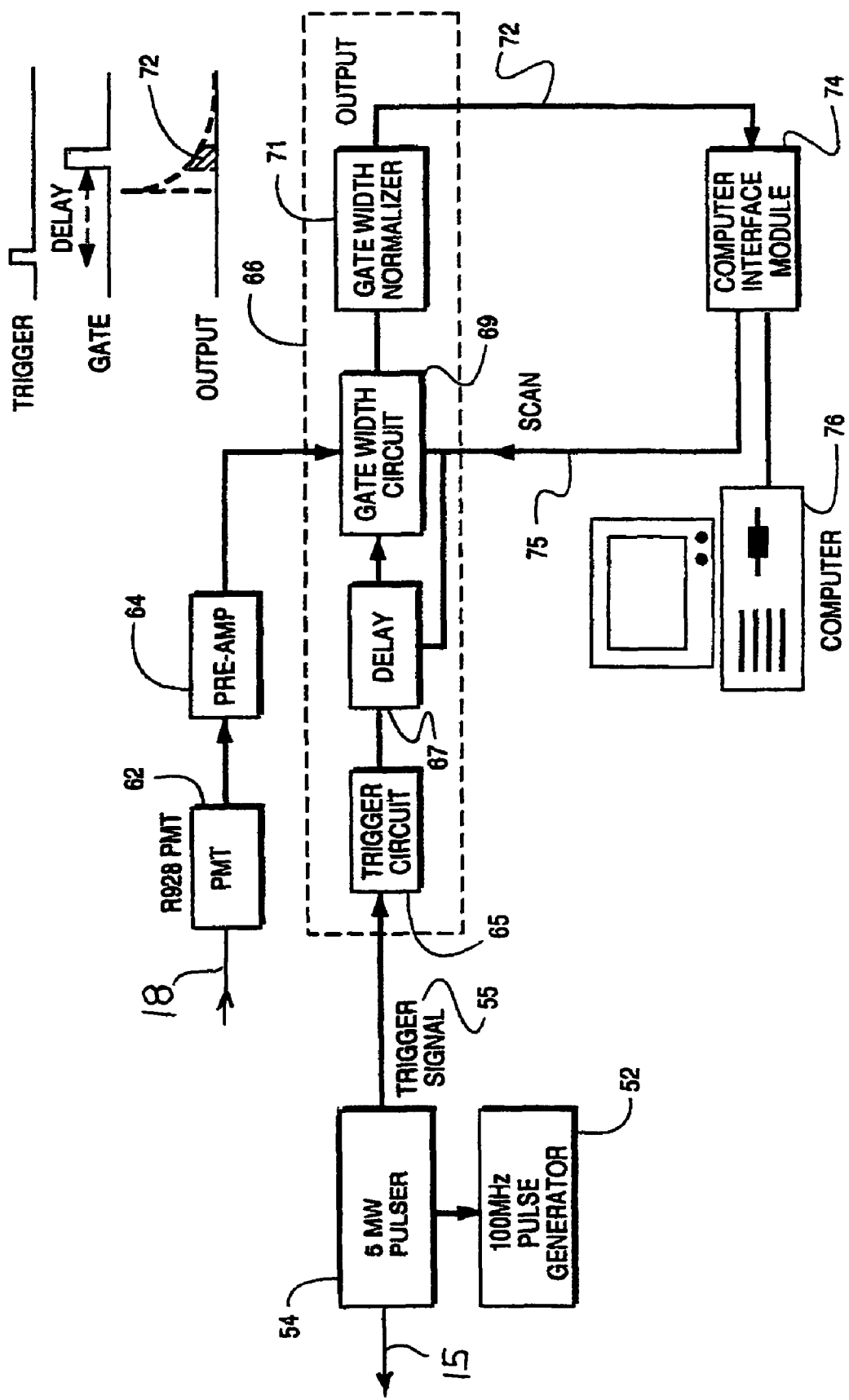

FIG. 4 shows diagrammatically the TRS system using a single "boxcar" integrator for the gated photon signal integration. A pulse generator 52 operating at a frequency on the order of 100 MHz connected to a pulser 52 drives a laser 54 (e.g., Hamamatsu PLP-10 pulsed laser diode). Laser 56 generates a train of light pulses of a selected wavelength (e.g., 754 nm) and constant duration on the order of 100 psec (Pulses of the order of a nanosecond can also be used). The light pulses are coupled to an optical fiber 58 and are introduced to subject 8. Transmitted photons migrate in the subject and arrive at a detection port of an optical fiber 60. In the migration process, the input pulse has been modified by the scattering and absorptive properties of tissue of subject 8. Photons arriving at the detection port are transmitted to a detector 62, (for example, Hamamatsu photomultipliers R928, R1517, MCP R1712, R1892 or ICCD commercially available from, for example, Jobin Yvon Inc., Edison, N.J. 08820).

Depending on which detector is used, the output of detector 62 may be amplified in a wide band preamplifier/impedance changer 64 and coupled to a boxcar integrator 66. Activated by a pulse gate, integrator 66 collects all arriving photons over a predetermined time interval. The integrator output (72) is sent to computer interface module 74. Computer 76 stores the total number of counts detected during the collection interval of integrator 66.

Integrator 66 includes a trigger 65 that is triggered by a signal 55 from pulser 54. Trigger 65 activates a delay gate 67 that, in turn, starts the counting of all detected photons during the time interval specified by a gate width circuit 69. Output from a gate width normalizer 71 is an analog signal or a digital signal representing all photons that arrived at the detection port during the preselected gate width interval. A suitable integrator can be achieved by using SR 250 manufactured by Stanford Research Systems.

Depending on the application, computer 76 sets the delay time of delay gate 67 and the gate width time of gate width circuit 69. The system can scan integration gate widths over the whole time profile of the detected pulse. Gate width normalizer 71 adjusts the width of the integration time depending on the detected signal level. The gate width may be increased logarithmically for smaller signals in accordance with the exponential decay of the fall of the detected pulse;

this increases the signal to noise ratio. The system operates at a repetition rate of at least 10 KHz.

Figure 4A:
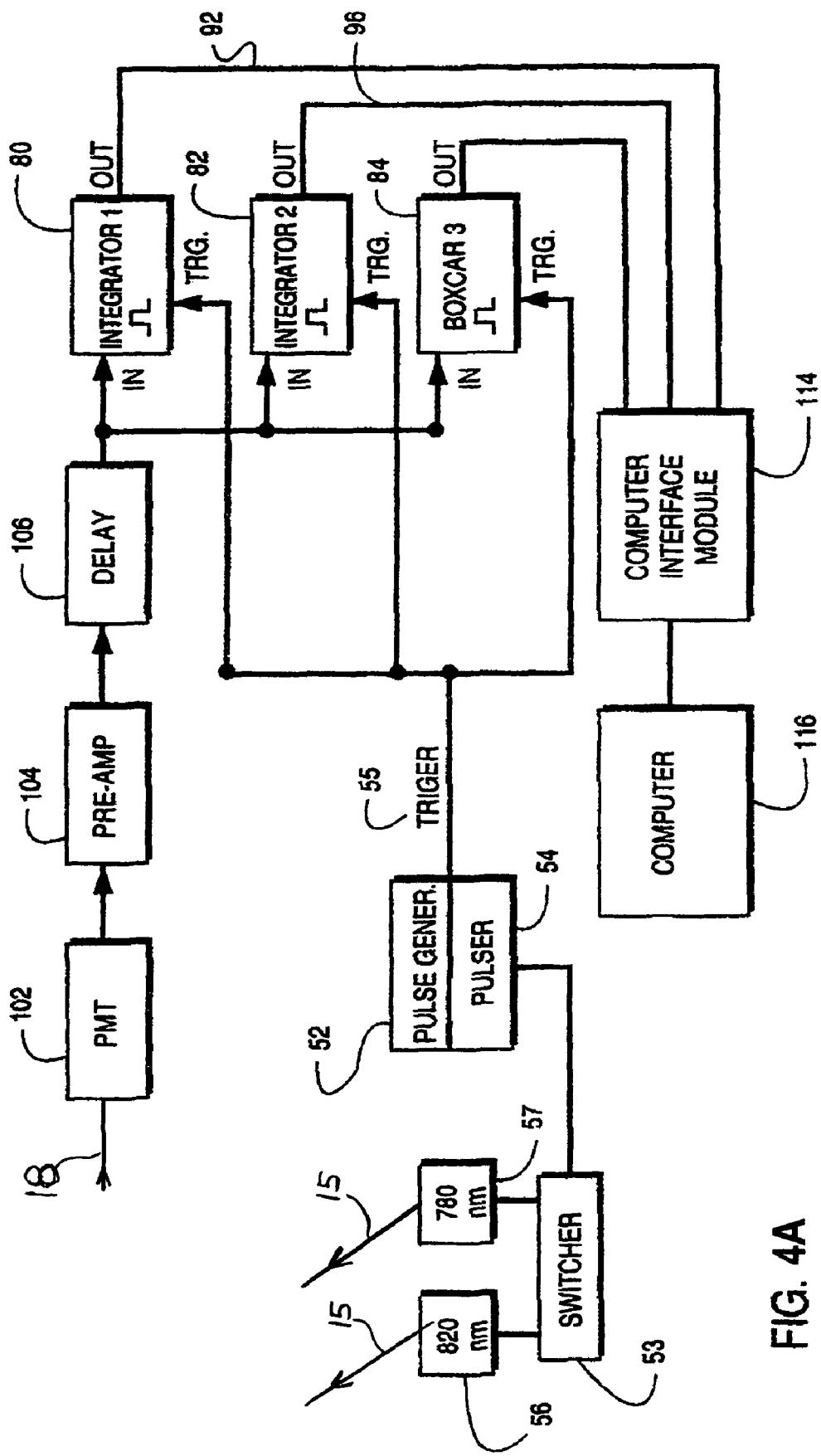

Referring to FIG. 4A, alternatively, the TRS system uses multiple, parallel integrators arranged in a faster and more efficient system. This system, just as the system of FIG. 4, may be used to determine the whole profile of the detected pulse shown in FIG. 4C, by appropriately selecting the delay gates and the gate widths shown in FIG. 4B. Pulse generator 52 connected to a pulser 54 drives alternately lasers 56 and 57. The alternate coupling is provided by a switcher 53 that operates at frequencies on the order of $10^7$ Hz. Pulses of light of wavelengths in the visible or infra-red range and duration in the range of about several nanoseconds to picosecond are generated. These light pulses are alternately coupled to subject 8. The light pulses are modified by tissue of subject 8 and are detected by detector 102.

The detected signal is amplified by preamplifier 104. Integrators 80, 82, and 84 collect data during selected gate width intervals, as shown on the timing diagram of FIG. 4B. Trigger 55 correlated with the input pulse 55A, triggers delay gates 1, 2, and 3 (shown in FIG. 4B) that are set to have selected delay times. Each delay gate then triggers its corresponding integrator that collects all photons arriving at the detector during the delay width time. Each integrator collects photons arriving at the detection port during its integration time defined by the gate width. This configuration can achieve a repetition rate of at least 10 kHz. The TRS system can separate the detected "useful" photons (which have migrated in the examined tissue) from the specular or surface-scattered photons that arrive much earlier since they are not delayed by the photon migration in the examined tissue.

Figure 4B:
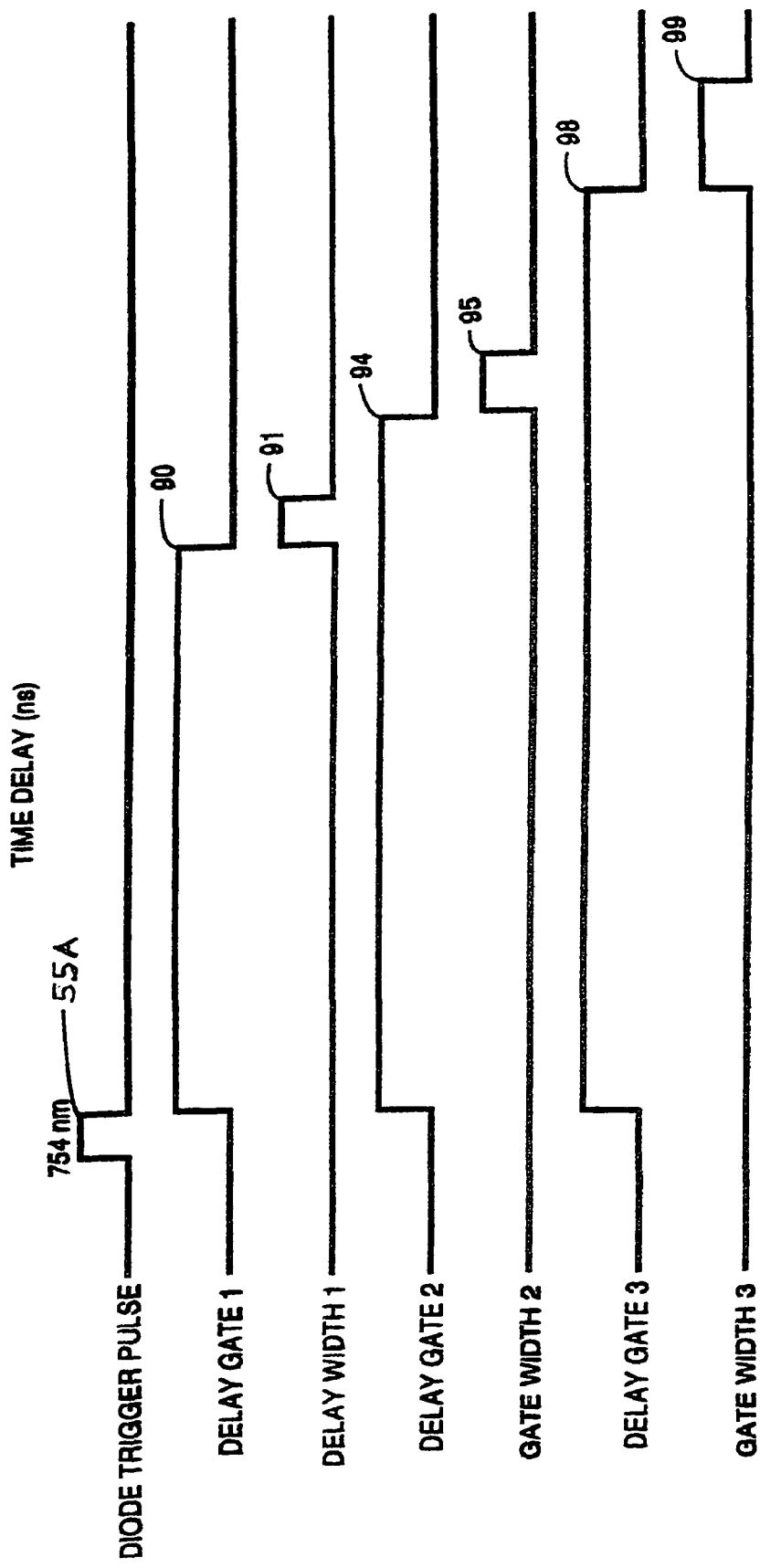
Figure 4C:
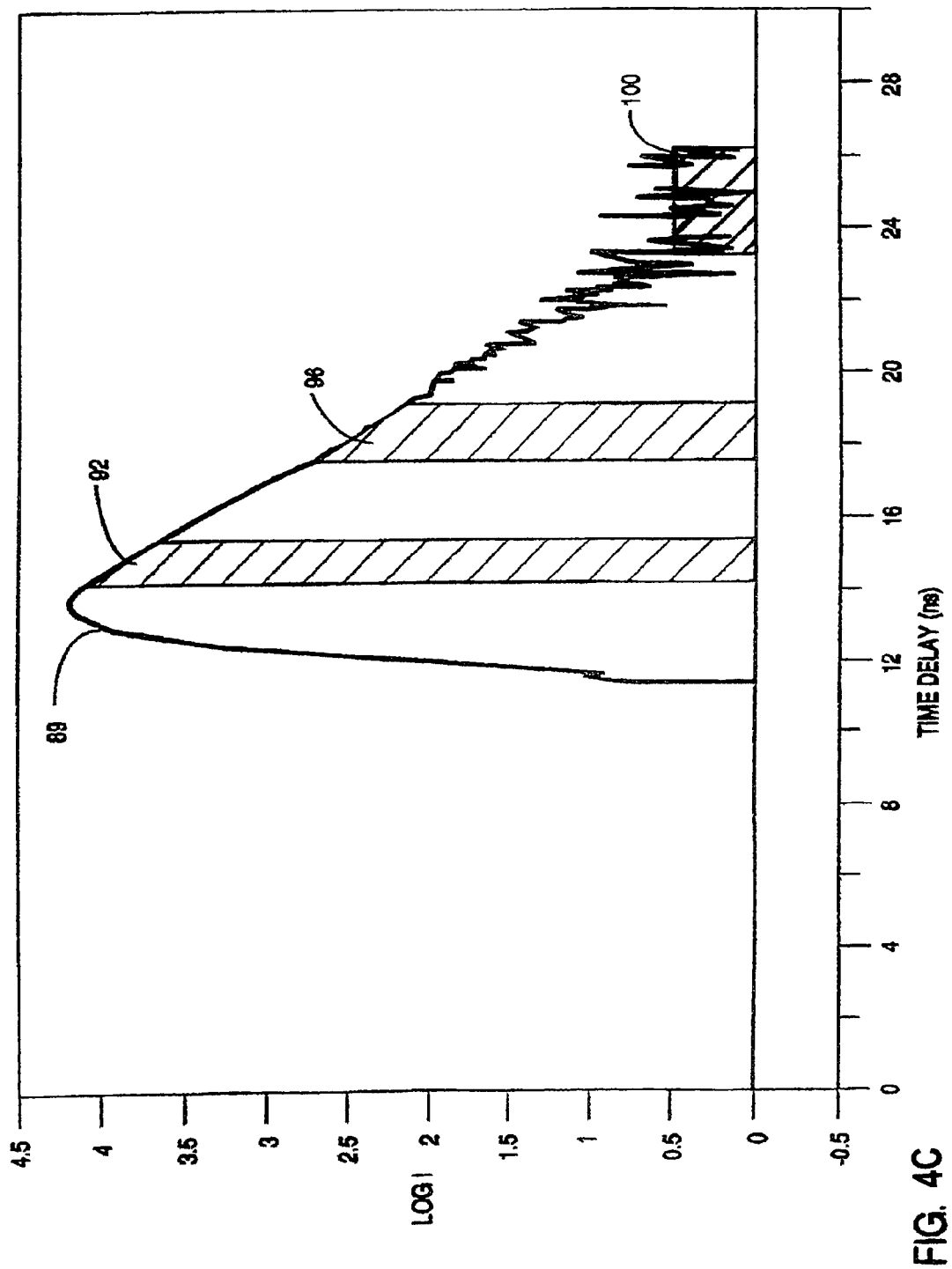

Referring to FIG. 4B, the TRS system uses the gate arrangement including gates 91 and 95 timed to detect the decay slope of the signal shown in FIG. 4C, while the third gate 99 may be used to determine the background signal shown as region 100 in FIG. 4C. Outputs 92 and 96 of integrators 80 and 82 are used to calculate the slope. To obtain approximately equal signal-to-noise ratios in the individual integrators, the length of the time windows is tailored to an exponential decay of the signal intensity with a logarithmic increase in the gate width with delay time.

Referring to FIGS. 4B and 4C, by scanning the delay gates (90, 94, and 98) and appropriately adjusting the gate widths, the system collects data corresponding to the entire detected pulse; subsequently, the shape (89) of the detected pulse is then calculated, i.e., time dependent light intensity profile I(t) is determined. The detected pulse shape, I(t), possesses information about the scattering and absorption properties of the examined tissue, which are closely related to the distribution of photon pathlengths in the tissue. The optical field is a function of the input-output port separation ($\rho$) as well as the optical properties of the tissue (absorption coefficient, $\mu_a$, scattering coefficient, $\mu_s$, and the mean cosine of anisotropic scattering, g). The general diffusion equation is used to describe the photon migration in tissue, as described by E. M. Sevick, B. Chance, J. Leigh, S. Nioka, and M. Maris in Analytical Biochemistry 195, 330 (1991) which is incorporated by reference as if fully set forth herein.

The system utilizes a previously determined solution for the fluency distribution in an infinite media as a Green's function with near infinite boundary conditions, wherein the diffusion equation is solved for the intensity of detected light in the reflectance geometry, R($\rho$, t), or the transmittance geometry T($\rho$, d, t). In the reflectance arrangement in a semi-infinite media with the separation of the input and output ports on the order of centimeters the reflectance was determined using equations provided in the above publication.

The TRS system enables direct measurement of the absorption coefficient or the effective scattering coefficient (1−g). $\mu_s$, using the equations described in the above-publication or as described in detail in U.S. Pat. No. 5,386,827, which is incorporated by reference. As described in U.S. Pat. No. 5,386,827, the systems of FIGS. 4, 4A, or 5 enable direct, real-time output of the absorption coefficient $\mu_a$, tissue saturation (Y), average optical pathlength (<L>), and the scattering coefficient $\mu_s$. The absorption coefficient is quantified by evaluating the decaying slope of the detected pulse, as shown in FIG. 6.

As stated above, the intensity profile of the detected pulse, I(t), is strongly dependent on the absorption and scattering properties of the examined tissue. For a relatively homogeneous tissue (e.g., breast tissue), the detected pulse, in general, exhibits a single exponential decay. In cases wherein the light pulse migrates through different types of tissues (e.g., brain tissue, which includes white matter and gray matter), the detected profile (I(t)) includes "two or more superimposed pulses", each characteristic of one type of tissue. The TRS system of FIG. 4 can scan the delay gates over the entire arrival time delay of the migrating photons to collect and deconvolute the intensity profile, I(t). A computer processor then fits iteratively the intensity profile to two or more overlapping curves and determines the scattering and absorption coefficients for each tissue effectively using Eqs. (3) and (5) provided in U.S. Pat. No. 5,386,827.

In the TRS system that includes two wavelengths sensitive to hemoglobin (Hb) and oxyhemoglobin (HbO$_2$) (e.g., 754 nm and 816 nm), the hemoglobin saturation (Y) is calculated by taking the ratio of absorption coefficients and using the equation 8 provided in U.S. Pat. No. 5,386,827 for the oxygen saturation.

In the studies of the brain, the TRS-pulse system is used to obtain the scattering ($\mu_s$ and absorption ($\mu_a$) coefficients of the white and gray matter at each wavelength. The absorption factors are used to determine oxygen saturation which is then used to detect hypoxia, localized bleeding and other reversible or irreversible disorders. The scattering changes in the examined tissue could be a manifestation of periventricular hyperintense syndrome (PVH), Alzheimer's disease manifested as plaques and tangles embedded in the gray matter and others.

As implied in the earlier description, it is desirable to precisely determine the delay time of the detected pulse. In the systems of FIGS. 4 and 4A, the pulser sends directly a trigger signal to each boxcar integrator.

Figure 5:
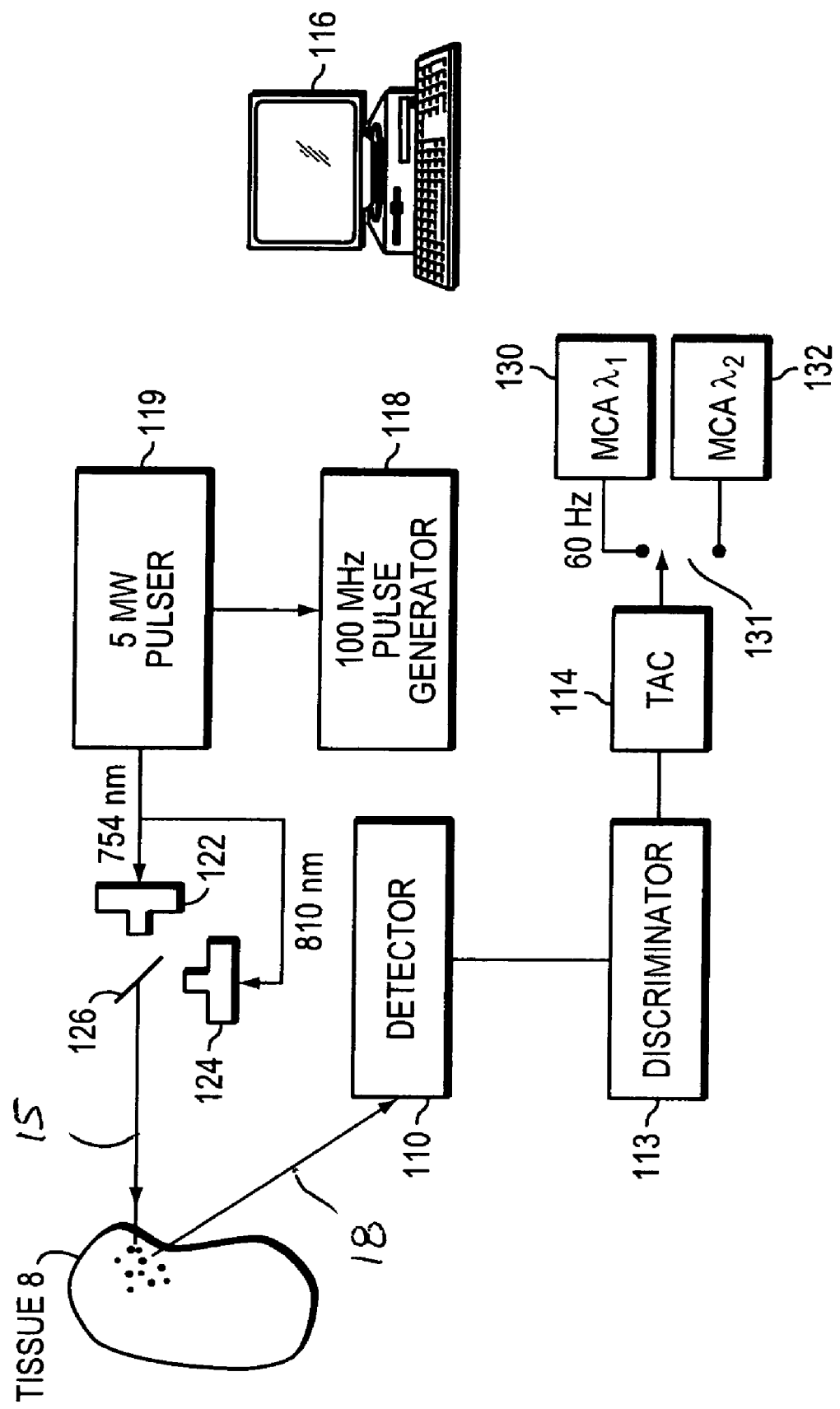
FIG. 5 is a schematic block diagram of another embodiment of a TRS system utilizing single photon counting electronics.
Figure 5A:
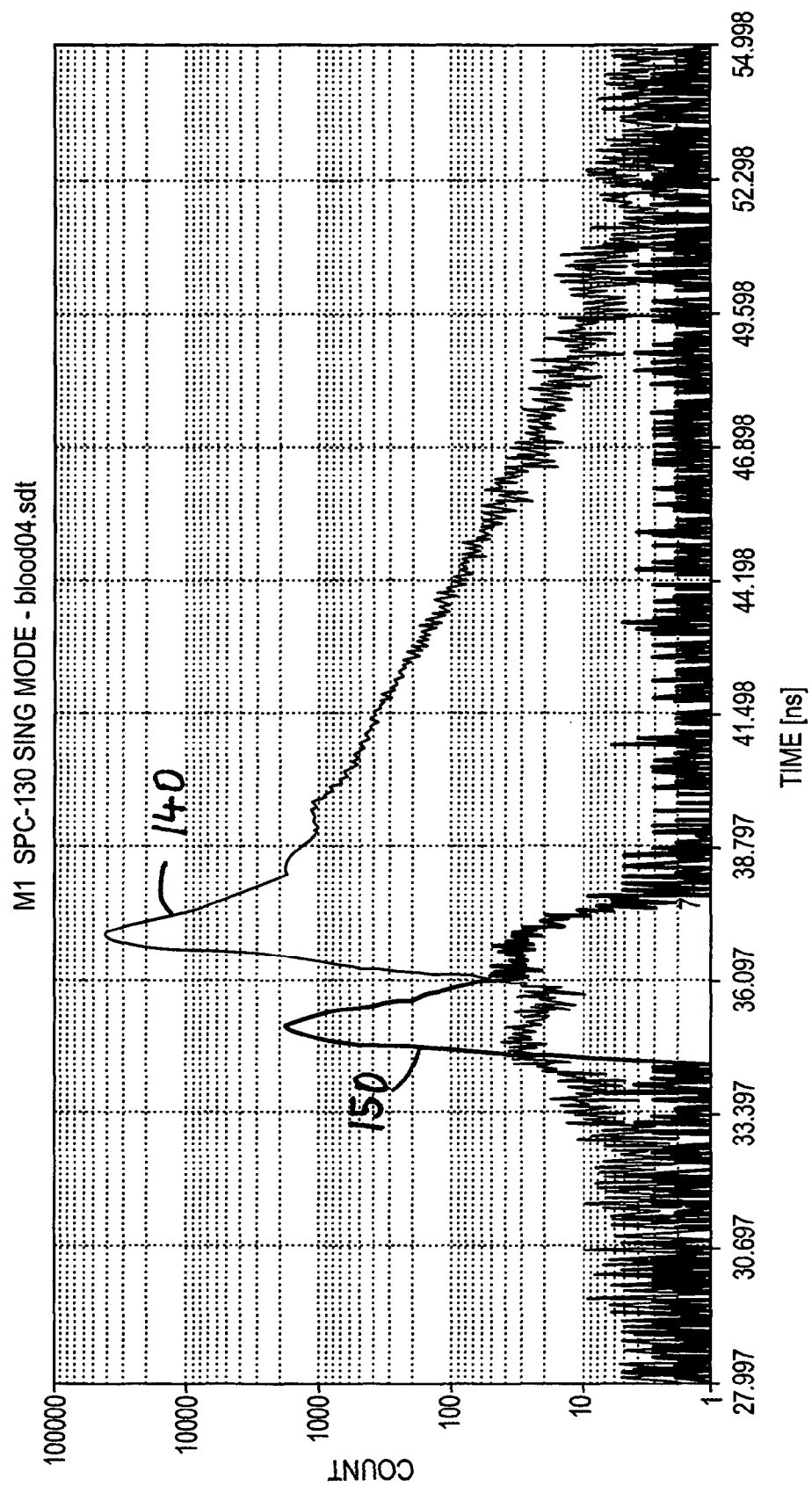
FIG. 5A is a time resolved spectrum measured by the TRS system of FIG. 4 or 4A, which spectrum includes a modified pulse and a reference pulse.
Figure 6:
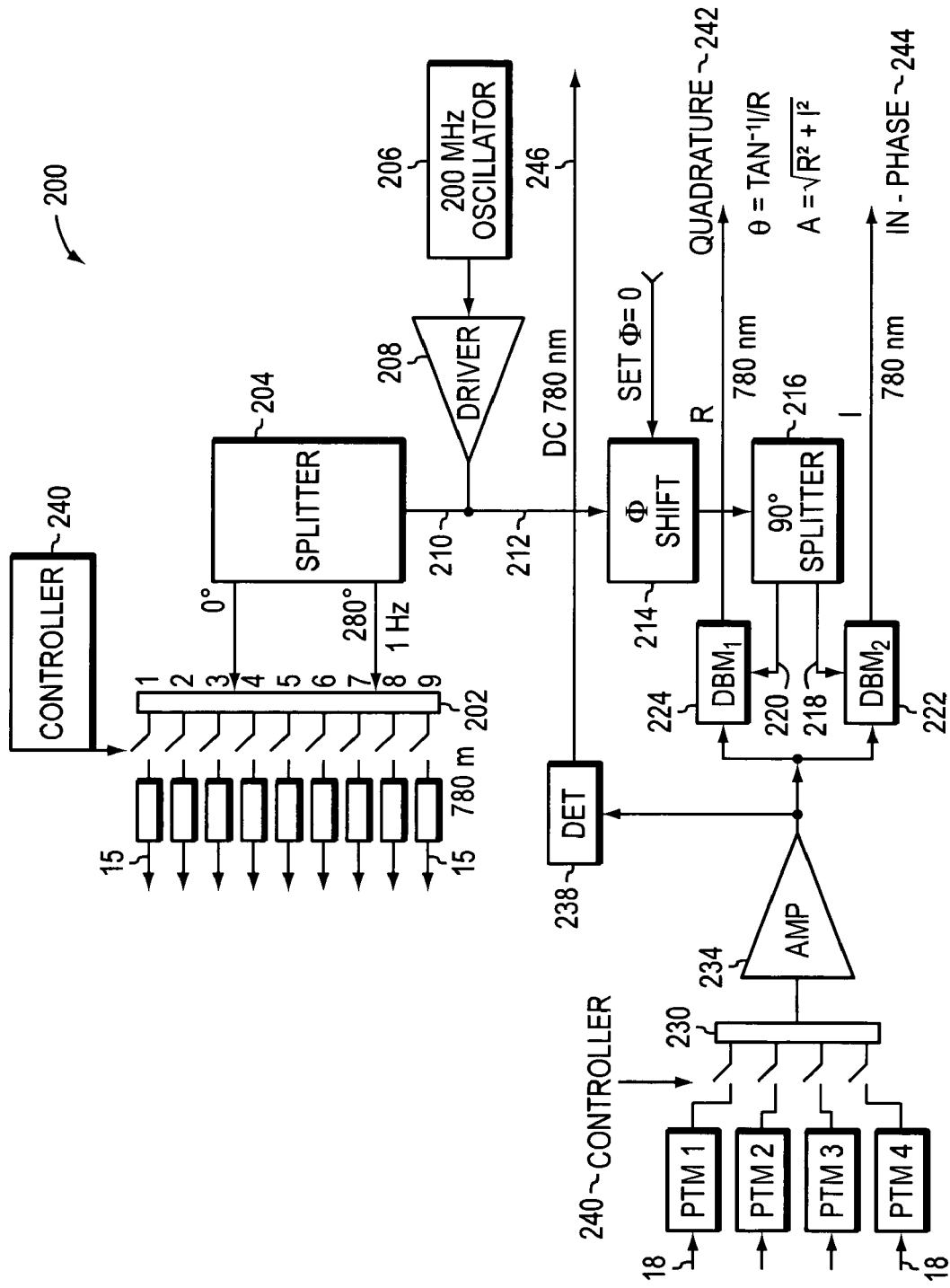
FIG. 6 shows schematically a homodyne phase-modulation system used for non-contact optical examination or imaging.

FIG. 5 shows a block diagram of the dual wavelength TRS system using single photon counting electronics. Laser diodes 122 and 124 (e.g., Hamamatsu PLP 10 laser diode) are driven by a 100 MHz pulse generator 118 connected to a 5 mW pulser 119. The light beam from laser 122 or laser 124 may be directed toward the tissue region of interest, or may be time shared electro-mechanically as shown in FIG. 5. Specifically, a vibrating mirror 126 (e.g., operating at 60 Hz synchronously with a switch 131) is used to deliver alternately the laser beam to the tissue region of interest.

Referring still to FIG. 5, after the illumination of the tissue region of interest, photons migrate over scatter paths inside the examined tissue and exit the tissue surface. A photodetector 110 (e.g., a photomultiplier) collects at least a portion of the exiting photons. The output of photomultiplier tube 110 is directly connected to a wide band amplifier 112 with appropriate roll-off to give good pulse shape and optimal signal to noise ratio. A high/low level discriminator 113 receives an output signal from amplifier 112. Discriminator 113 is a pulse amplitude discriminator wherein the threshold for acceptance of a pulse is a constant fraction of the peak amplitude of the pulse. Next, the discriminator pulses are sent to a time-to-amplitude convertor (TAC) 114.

The time-to-amplitude converter produces an output pulse with amplitude proportional to the time difference between start and stop pulses. The pulse-photon detection cycle is repeated at a frequency on the order of 10 MHz to acquire a typical photon distribution. The multichannel analyzer collects only a single photon for each input light pulse. Signal from each detected photon is encoded for time delay and recorded. Following the time to amplitude conversion, the counts corresponding to the two wavelengths are separately summed in two multichannel analyzers (MCA) 130 and 132, respectively. Each multichannel analyzer collects and stores the time-resolved spectrum that consists of detected pulse (140) modified by the examined tissue and a reference pulse (150 in FIG. 5A) collected by a reference fiber. The delay of the reference pulse in FIG. 5A is much smaller and is shown for pulse shape comparison only. (The system may use a reference fiber of a known length, coupling the light source and detector for detecting and collecting a reference pulse spectrum, as shown in FIG. 5A).

In general, the TRS systems of FIGS. 4, 4A, and 5 provide nanosecond or picosecond laser illumination of a tissue region that is distant from the light source by 1, 2 or more meters permitting non-contact activation of photon migration. The detector system images the object illuminated using a large 10×10 cm lens which gives a viewing angle of approximately 10 degrees. In order to distinguish reflected light from diffusing light, short pulses are used, shorter than few a nanoseconds and preferably three tenths of a nanosecond.

The emerging signal consists of any leakage from the source to the detector in the time domain of three tenths of a nanosecond. (Traveling through space at 30 picoseconds equals 1 cm) Thereafter, 3 or more nanoseconds later, the first specular reflections from the tissue are observed as shown in FIG. 5A. Numerous photons exit; in fact, a large fraction of them exit, but not all of them will exit in the direction of the objective lens. The diffusing photons then decay in intensity as they emerge farther and farther from the source impact point, as shown by the tail of curve 140 in FIG. 5A.

The detector is preferably an ICCD, since it can collect an image of the emergent photons from an area of several centimeters surrounding the point of impact of the input light (furthermore notice that it is usually not possible to measure photons emergent from the source position, in this case we have the advantage of doing this). The detected emergent photons can be integrated over the area of the ICCD detector. The information the TRS data is in the slope of the logarithm of the intensity against the arrival time (in nanosec) according to the equation originally provided in "Time-resolved reflectance and transmittance for the noninvasive measurement of tissue optical properties" by M. S. Patterson, B. Chance, and B. C. Willson, Appl. Optics Vol. 28, 2331-2336 (1989). Thus, the detected spectrum provides directly the absorption coefficient of the biological tissue in which the photons have migrated.

Referring to FIG. 6, in another embodiment, a homodyne phase modulation system 200 is used instead of the above-described examination and/or imaging systems. Phase modulation system 200 provides signal to a non-contact optical probe 12 (shown in FIG. 1) from one or several light sources (e.g., photodiodes or diode lasers) and detects light by one or several detectors (e.g., PMT or avalanche diode). For example, one source and detector pair may be used for one wavelength in the range of visible to infrared light (e.g., 650 nm to 900 nm). Each detector also includes an interference filter, which is important especially when the system detects excited fluorescent light. If several sources and detectors are used at the same time, the signal may be phase or frequency encoded to improve resolution in case of parallel tissue examination.

The PMS system 200 employs homodyne phase detection. A switch 202 connects, for example, laser diodes $S_1, S_2, \ldots, S_9$ to a phase splitter 204, which provides to the diodes an RF modulation signal having both a 0 degree phase and a 180 degree phase. Imaging system 200 also includes a 200 MHz oscillator 206 providing RF signal to a driver 208, which is connected to phase splitter 204. (Alternatively, an oscillator in the range of 10-1000 MHz, preferably 50-500 MHz, may be used.) A phase shifter 214 receives the drive signal (212) from driver 208 and provides the signal of a selected phase (e.g., a 0° phase change) to a 90° phase splitter 216. Phase splitter 216 provides a 0° phase signal (218) and a 90° phase signal (220) to double balance mixers (DBM) 222 and 224, respectively.

A controller 240, connected to a personal computer (PC), sequences laser diodes $S_1, S_2, \ldots, S_9$ using switch 202 so that two diodes receive modulate signal at a 0° phase and a 180° phase from splitter 204. At the same time, a controller 240 connects a symmetrically located PMT using a switch 230 to an amplifier 234. Amplifier 234 provides a detection signal to double balance mixers 222 and 224, and to a DC detector 238. Double balance mixer 222 receives the detection signal and the 0° phase reference signal (218) and provides an in-phase signal I (244). Double balance mixer 124 receives the detection signal and the 90° phase reference signal (220) and provides a quadrature signal R (242). DC detector 238 provides DC signal (246). The in-phase signal I and quadrature signal R specify the phase ($\theta=\tan^{-1}I/R$) of the detected optical radiation and the amplitude ($A=(R_2I_2)_{-1/2}$) of the detected optical radiation. This phase detection circuit was described in U.S. Pat. No. 5,553,614, which is incorporated by reference.

Optical system 200 directs controller 240 to sequence the laser diodes and the PMT detectors using an appropriate timing diagram. Alternatively, several sources and detectors are used in parallel using frequency encoding. The computer stores the phase value and the amplitude value measured for each of the source detector combinations for calculating blood volume, oxygenation, or scattering coefficient. The computer can also generate images described below.

Figure 6A:
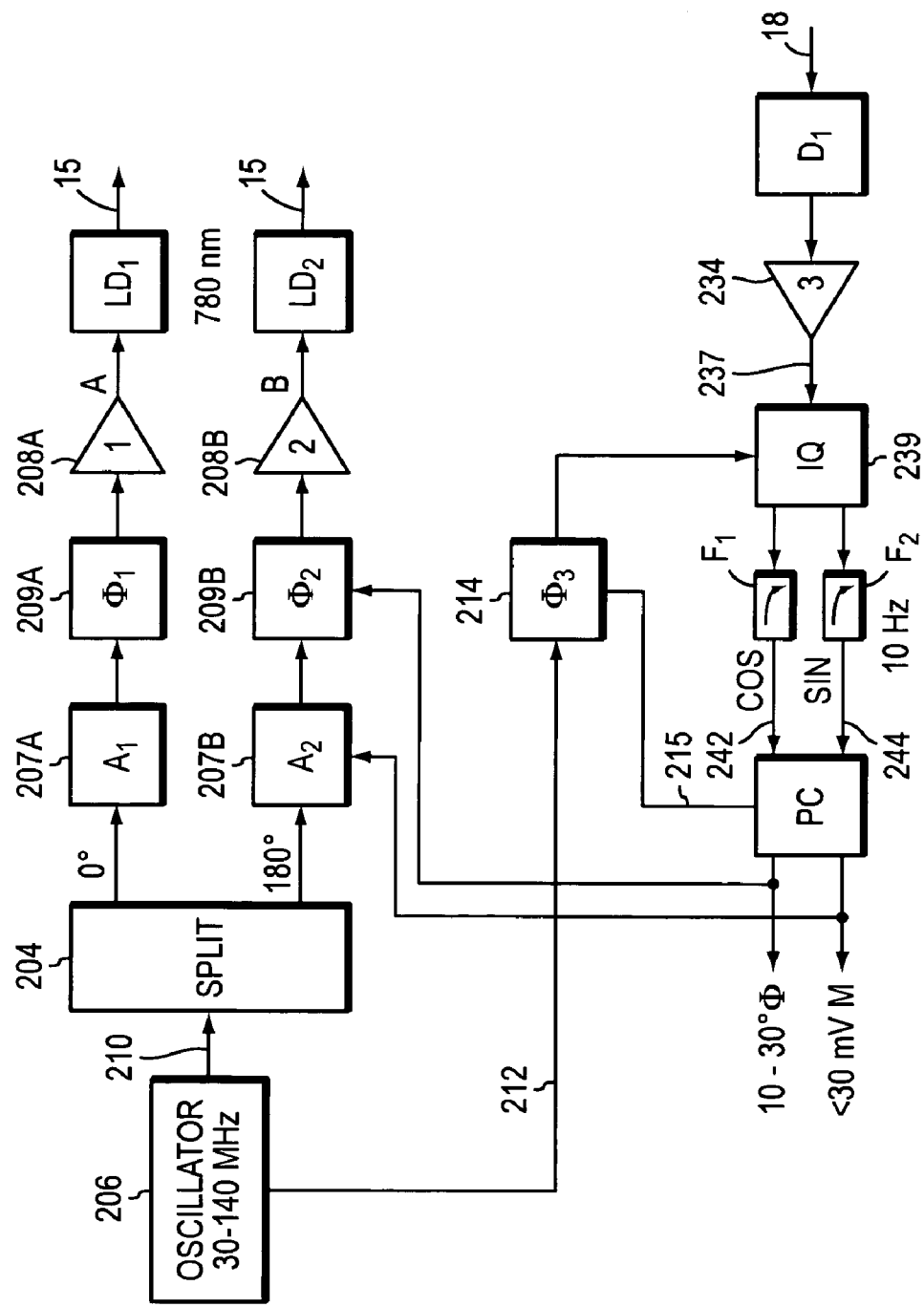
FIG. 6A shows schematically another homodyne phase-modulation system used for non-contact optical examination or imaging.

FIG. 6A shows diagrammatically one portion of phase cancellation, phased array imaging system 200. The depicted portion of imaging system 200 includes two laser diodes $LD_1$, and $LD_2$ and a light detector $D_1$ optically coupled to non-contact optical probe 12. Oscillator 206 provides carrier waveform having a frequency in range of 30 to 140 MHz. The carrier waveform frequency is selected depending on the operation of the system. When time multiplexing the light sources using switch 202, then the carrier waveform is modulated at a lower frequency, e.g., 30 MHz to afford switching time.

When no time multiplexing is performed, oscillator 206 operates in the 100 MHz region. Splitter 204 splits the oscillator waveform into 0° and 180° signals that are then attenuated by digitally controlled attenuators 107A and 107B by 0% to 10% in amplitude. The phase of the attenuated signals is appropriately shifted by digitally controlled phase shifters 209A and 209B in the range of 10°-30° and preferably 20° in phase. Laser drivers 208A and 208B drive $LD_1$ and $LD_2$, respectively, which emit light of the same wavelength, for example, 780 or 800 nm. After the introduced light migrates in the examined tissued, a PMT detector $D_1$ amplifies the detected signals having initially the 0 and 180° phases. As described above, for homogeneous tissue and symmetric locations of $LD_1$, $LD_2$ and $D_1$, the output of the PMT is 90°, i.e., halfway between 0° and 180° and the amplitude is close to zero. The personal computer (PC) adjusts the attenuation provided by attenuator 207B and the phase shift provided by phase shifter 209B so that detector $D_1$ detects phase nominally around 25° and amplitude nominally around $\leq$10 millivolts for homogeneous tissue. This signal is connected to amplifier 234 and to the IQ circuit 239. The cosine and sine signals are fed into the personal computer, which takes the amplitude (the square root of the sum of the squares of I and Q) and the phase angle (the angle whose tangent is I/Q) to give outputs of phase around 25° and amplitude signals around 10 millivolts. The personal computer also adjusts the reference signal to the IQ to have the phase $\phi_3$ between 10° to 30° and preferably around 25°, i.e., phase shifter 214 provides to the IQ circuit 239 the reference phase having a value selected by the combination of phase shifters 209A and 209B.

Splitter 204 may be a two way 180° power splitter model number ZSCJ-2 1, available from Mini-Circuits (P.O. Box 350186, Brooklyn, N.Y. 11235-0003). The phase shifters 209A, 209B and 214 and attenuators 207A, and 207B are also available from Mini-Circuits, wherein the attenuators can be high isolation amplifier MAN-1AD. IQ demodulator 239 is a demodulator MIQY-140D also available from Mini-Circuits.

The system obtains the initial values of attenuator 207B ($A_2$) and phase shifter 209B ($\phi_2$) on a model or a symmetric tissue region (e.g., the contralateral breast or kidney or another region of the same organ that is tumor free). The non-contact probe may be calibrated on a tissue model by storing the calibration values of $A_2$ and $\phi_2$ for the various source-detector pairs (e.g., for different wavelenghts, to obtain baseline values or a baseline image). The noncontact probe is then directed to the examined breast or abdomen, for example, and the phases and amplitudes are detected for the various source and detector combinations. When the contralateral "tumor free" kidney is used as a model, the probe is transferred to the contralateral kidney (taking note to rotate the probe because of the mirror image nature of the kidney physiology) and then the images are read out from all the source-detector combinations to acquire the tissue image.

There is no limitation on multiplexing as long as the bandwidth of $F_1$ and $F_2$ is recognized as being the limiting condition in the system normalization. It should be noted that normalization must be accurate and without "dither" and therefore, a significant amount of filtering in $F_1$ and $F_2$, i.e., less than 10 Hz bandwidth. If $\phi_2$ is adjusted over a large range, there will be an amplitude-phase crosstalk. Thus, the system may adjust phase and then amplitude and repeat these adjustments iteratively because of the amplitude phase crosstalk. The control of $A_1$ and $100_1$ provides even a greater range of control, where obviously inverse signals would be applied to them, i.e., as the $A_1\phi_1$ signals are increased, the $A_2$, $\phi_2$ signals would be decreased. Both $A_2$ and $\phi_2$ can be controlled by PIN diodes, to achieve an extremely wideband frequency range. However, since signal processing controls the bandwidth of the feedback system, that either PIN diode or relay control of the phase and amplitude is feasible for automatic compensation. If dual wavelength or triple wavelength sources are used, each one of them is separately calibrated for the intensity and position relative to the examined or imaged tissue.

The PMS system separates the detected "useful" photons from the "unwanted" specular or surface-scattered photons computationally by a Fourier transform on all detected data. That is, the TRS system separates the detected "useful" photons (which have migrated in the examined tissue) from the "unwanted" specular or surface-scattered photons by adjusting the detection gates to eliminate the photons that arrive much earlier (i.e., to eliminate photons that are not delayed by the photon migration in the examined tissue.). As described in the above-cited publications, the detected PMS signal (in the frequency space) corresponds to the detected TRS signal (in the time space) via a Fourier transformation. Therefore, the detected PMS signal (including both the "useful" photons and the "unwanted" photons) is Fourier transformed from the frequency domain to the time domain. Then, the processor eliminates the initial portion corresponding to the "early" arriving photons. The "later" arriving photons had migrated in the examined tissue and thus carry information about the tissue properties.

As described above, the optical data can be collected over two symmetrical tissue regions (e.g., the left breast and the right breast, or two symmetrical brain lobes expected to have the same optical properties for normal tissue). Any difference in the optical properties corresponds to a tissue abnormality (e.g., bleeding or tumor), or different functional use of the brain tissue manifested as changes in blood oxygenation or in a blood volume in the examined tissue. For example, tapping with fingers of the right hand can be functionally detected in the left brain hemisphere. The "functional" data can be compared to the rest data to obtain a baseline image. The optical data sets are processed using an imaging algorithm, for example, a back projection algorithm known in computed tomography (CT).

The collected data sets are processed using an imaging algorithm. The imaging algorithm calculates the blood volume of the examined tissue for each source-detector combination for each data set. The imaging algorithm can also calculate the oxygenation of the examined tissue for each source-detector combination.

The blood volume or oxygenation images can be subtracted from "model" images. The blood volume image can be subtracted from the oxygenation image to create congruence data (further described below) to localize and characterize a tissue anomaly. The imaging algorithm may also create an image using the differential image data sets. Prior to creating the image, an interpolation algorithm is employed to expand the differential image data set, containing 16 (4×4) data points, to an imaging data set containing 32×32 image points.

Alternatively, the computer uses a back projection algorithm known in computed tomography (CT) modified for light diffusion and refraction and the banana like geometry employed by the optical imaging system. In the optical back projection algorithm, the probabilistic concept of the "photon migration density" replaces the linear relationship of ballistically transmitted X-rays, for the beam representing pixels. The photon migration density denotes a probability that a photon introduced at the input port will occupy a specific pixel and reach the detection port. For different types of tissue, the phase modulation spectrophotometer provides the values of the scattering and absorption coefficients employed in the probability calculations. (These values are determined as described in U.S. Pat. No. 5,402,778, which is incorporated by reference) In the image reconstruction program, the probability is translated into a weight factor, when it is used to process back projection. The back projection averages out the values of information that each beam carries with the weighting in each pixel. The specific algorithms are provided in U.S. Pat. No. 5,853,370 issued on Dec. 29, 1998.

A method for correcting blurring and refraction used in the back projection algorithm was described by S. B. Colak, H. Schomberg, G. W.'t Hooft, M. B. van der Mark on Mar. 12, 1996, in "Optical Back projection Tomography in Heterogeneous Diffusive Media" which is incorporated by reference as if fully set forth herein. The references cited in this publication provide further information about the optical back projection tomography and are incorporated by reference as if fully set forth herein.

The above described non-contact systems provide the possibility of examining brain function or interrogation of a large number of people; for example, in line for baggage check in an airport. As described in U.S. application Ser. No. 10/618,579, which is incorporated by reference, the examined individuals may be asked to answer several security questions (e.g., "Did anybody else pack your luggage?") displayed on a computer terminal. As the individuals are looking at the computer terminal, there is a spectroscopic system with a source and a detector for brain examination. The non-contact spectroscopic system can use a number of wavelengths in the NIR region, presumably those emphasizing the less visible light, at 780 nm, 805 nm, or 850 nm.

Pursuant to an approval (if required), each individual may be surveyed by a gated CCD camera that images the forehead, including separately the facial expression. This system tracks various individuals who are giving extraordinary oxygenation and or blood signals measured by any of the above-referenced spectroscopic systems, suggesting "suspicious" mental activity. Since the check-in lines often last ½ hour, any particular person might be tagged for more detailed studies or other studies could be accomplished separately.

As described in U.S. application Ser. No. 10/618,579, the spectroscopic system creates separate images for blood volume and blood oxygenation. The images include numerous voxels of data generated using histograms or other methods known in the art. The spectroscopic system is then used as a "deceit measure detector" by checking for a specific signal at one or several signature voxels for lying (e.g., examining blood volume and signal) when the subject is lying while answering questions provided at the check-in line at the airport. On the other hand, the system detects a weak signal at the signature voxel when the subject is telling the truth. The system can design automatically questions displayed at the computer terminal, where the answer is known to provide "control images" for each person. For example, based on the booked airline ticket, the system asks questions related to the name, address, sex and other known information about the individual. (In the image, the system looks for extraordinarily high blood volume or oxygenation signals and their possible congruence as described in PCT Application PCT/US99/03030, which is incorporated by reference.

Figures 7, 7A:
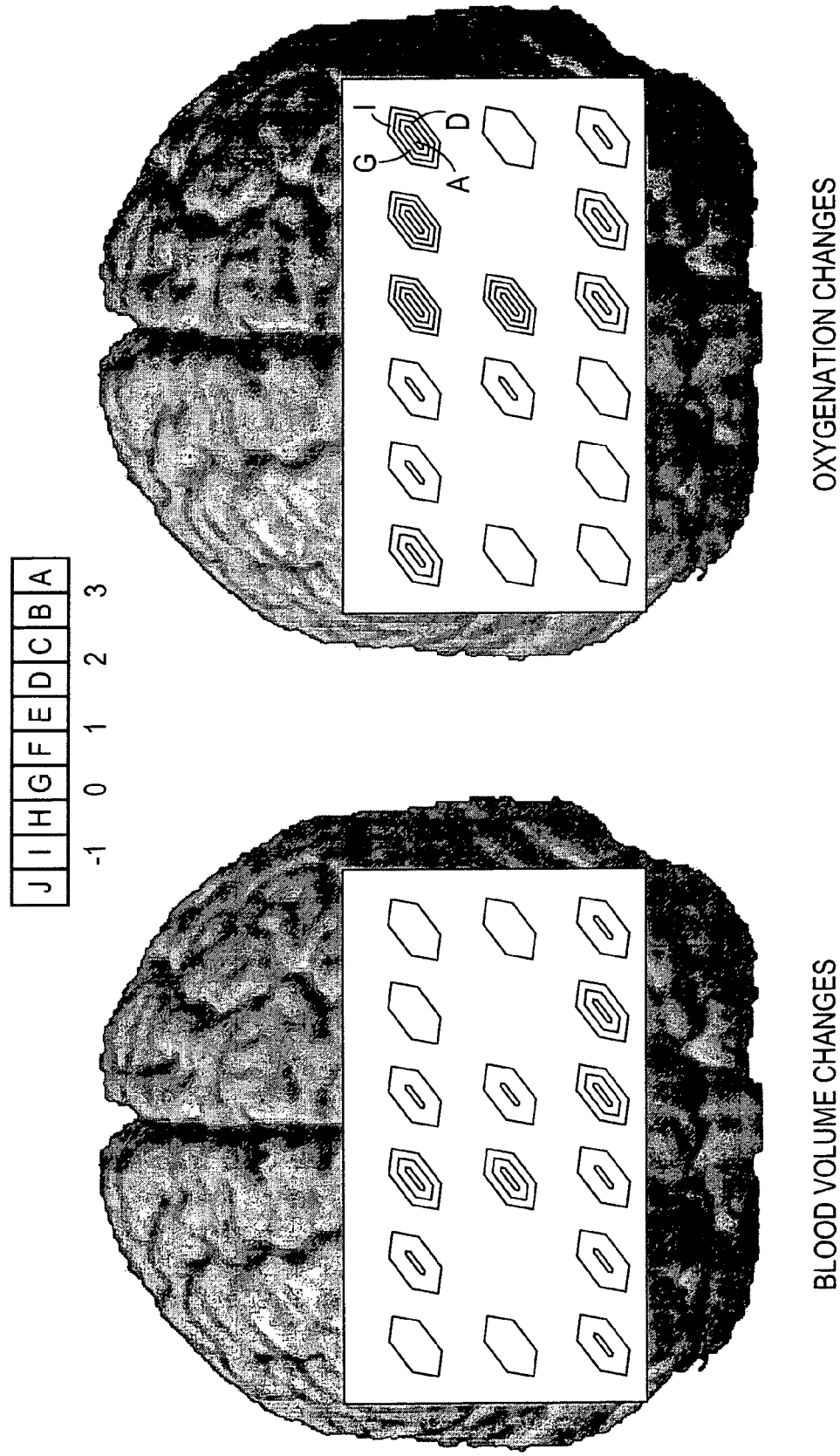
FIGS. 7 and 7A show optical images corresponding to blood volume changes and oxygenation changes, in the frontal lobe, when solving 8 letter anagrams by a human subject.
Figure 7C:
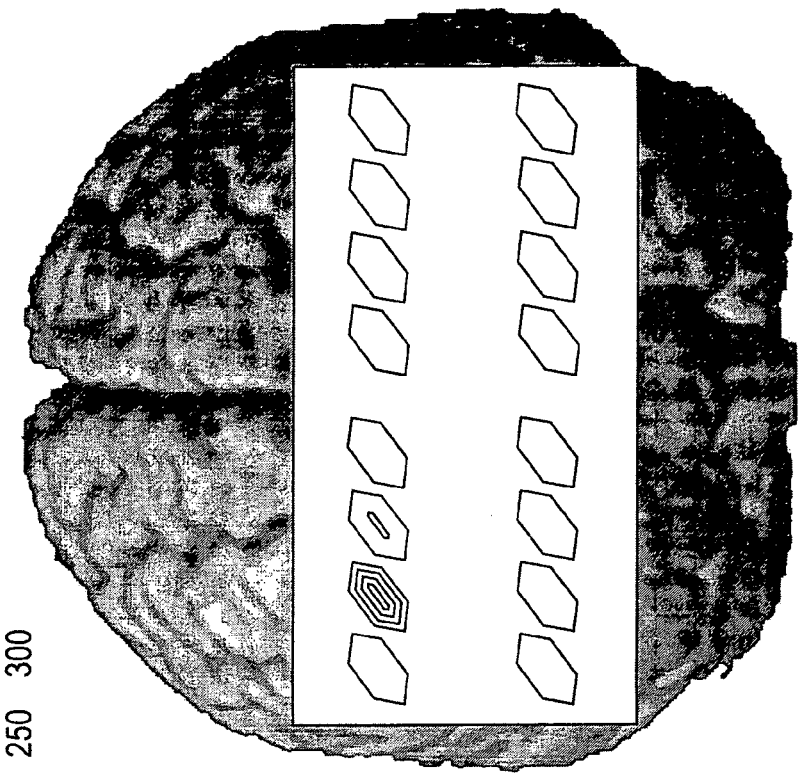
FIGS. 7B and 7C show optical images corresponding to oxygenation changes, in the frontal lobe, when the examined subject tells a lie and the truth, respectively.
Figure 7B:
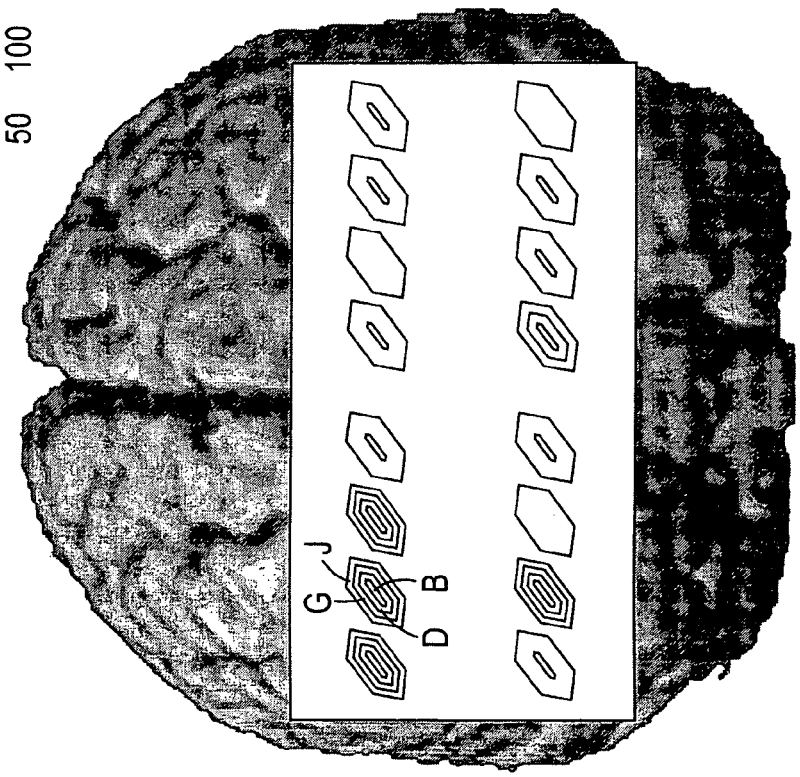
Figure 7D:
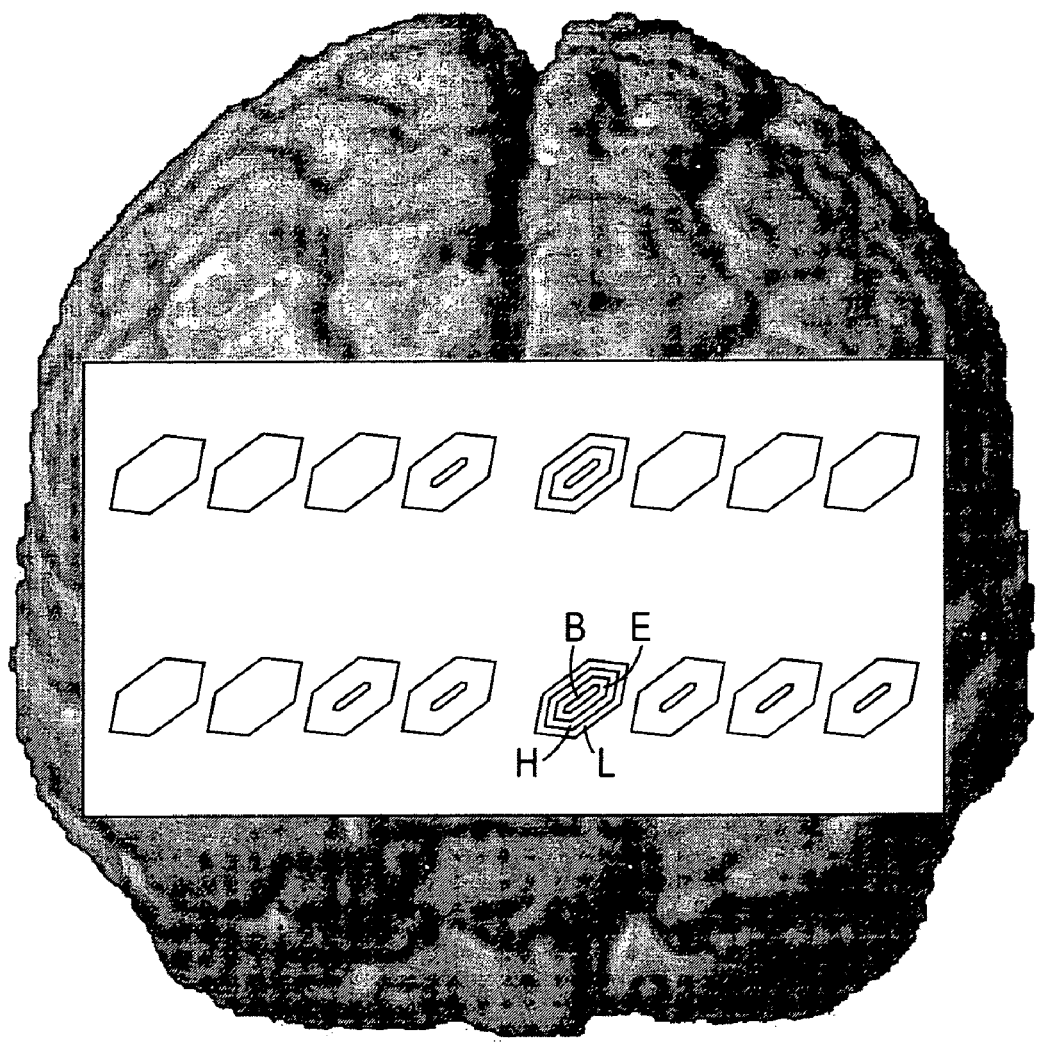
FIG. 7D shows a sudden insight optical image for oxygenation changes, in the frontal lobe, 15 seconds after solving an anagram minus 15 seconds before solving the anagram.

FIGS. 7, 7A, 7B, 7C and 7D show optical images of the frontal lobe generated by the optical system of FIG. 1 described in the co-pending U.S. application Ser. No. 10/618,579 (incorporated by reference). The contactless optical system 10 (FIG. 1) can generate similar images. FIGS. 7 and 7A show optical images corresponding to blood volume changes and oxygenation changes, in the frontal lobe, when solving 8 letter anagrams by a human subject. FIGS. 7B and 7C show optical images corresponding to oxygenation changes, in the frontal lobe, when the examined subject tells a lie and the truth, respectively. FIG. 7D shows a sudden insight optical image for oxygenation changes, in the frontal lobe, 15 seconds after solving an anagram minus 15 seconds before solving the anagram.

Referring to FIGS. 7B and 7C, based on the detected intensity at each measured voxel of the image, the optical system can determine the "deceit" level corresponding to the answer of the examined subject. Generally, based on the "background" image of an individual, when an individual is telling the truth the oxygenation images include one or two highly pronounced voxels (FIG. 7C). When the examined individual is lying, the oxygenation images usually provide a large number of active voxels, as shown in FIG. 7B.

The above-described optical non-contact system may also be used at the security location to check for magnetic objects. While in the other two examinations, i.e. waiting for baggage check-in, or ticket check-in, ample time is available because the process can take respectively 30 minutes or 5 minutes, in the latter case taking into account that the rhetorical, "Have you had your baggage with you at all times?" has routinely been answered by a lie. In special security, which indeed should be curtained off (i.e. public examination is demeaning, and where the shoes are examined, etc.), it is certainly stressful and a few questions could certainly be asked and the response noted. Any person with a particular hat covering the forehead, or nodding their head during the scanning process so as to confound the image would immediately be suspect, and additional screening would be conducted.

According to another aspect of the present invention, the scanning system is a "radar-like" frontal surveillance system that includes not only close-up applications, for example, where a person is singled out and interrogated (for example, using the TRS system imaging his forehead with CCD camera technology). In this system, laser light is scanned over the person's forehead to obtain optimal signal-to-noise ratio of image data processed as described in Appendix A. The system provides diffuse illumination and background signals are minimized by standard radar techniques, for example, by moving target indication, which would select out anyone who is moving the head while in the security line and distinguish them from multiple reflection images.

As described above, the ICCD image acquisition is gated to receive light in the first 10 nsec. The system concentrates on the less visible NIR wavelengths, such as 780, 805 and 850 nm and is beset by multiple reflections of the excitation light from surrounding objects, which might be delayed sufficiently to obscure the photon migration signal from the forehead.

Alternatively, the system may generate an image using only ballistic photons, as known in the spectroscopic art. The detector need not be a CCD but could be a mosaic of detectors such as a multi-anode MCP multi-channel-plate detector, etc. And if, indeed, the photons are ballistic, it just means there is minimal scattering and an image taken with CW or phase would serve just as well. In fact, this might be the case where phase modulation imaging might come to the fore because it is so much simpler than the pulse time imaging.

Any of the above-described systems may be constructed as an attachment to notebook computers so that the user would be monitored for alertness by a flying spot scan over the forehead or an area of illumination taking advantage of the fact that a TRS system affords a time separation of the illumination pulse and the re-emitted light, as described above. For airport detection, the prefrontal imaging can occur either covertly or with consent. Advantageously, there is nothing to be "put on the subject" and the brain scan can start immediately where the subject is, for example, an examination booth or looking at a monitor. The same thing goes for an interrogation procedure, which is more convenient if the scanner is part of the interrogation procedure. Great care is taken so that the generated laser beam is not directed to the subject's eyes. The scanner can operate at room light since it would be in the NIR region and suitable filters would allow room light illumination in shorter wavelengths than NIR.

With respect to immobilization, this is not a high-resolution system and head motions of a few millimeters are quite acceptable, since we expect the activation to cover a significant area, 2-3 cm². However, in covert detection one would obviously have a TV system as well which would allow one to track the head and to shift the laser beam to illuminate the same spot or spots of the forehead regardless of movement.

Other embodiments are within the following claims:

The invention claimed is:

1. An optical system for examination of biological tissue, comprising:
   a light source for generating a light beam of a wavelength in a visible to infra-red range to be introduced in the biological tissue spaced apart from said source;
   a scanning and irradiation system constructed to receive said generated light beam and constructed to irradiate a tissue area of the biological tissue to be examined by scanning said light beam propagating in air, said scanning and irradiation system being spaced apart from the tissue area;
   a light detector located away from the examined biological tissue and constructed to detect light that has migrated in the examined biological tissue and has propagated in air from the examined biological tissue, said light detector providing detected optical data; and
   a computer controlled system including electronics for controlling said light source, said light detector and said scanning and irradiation system, said computer controlled system being constructed to separate reflected photons from photons that have migrated inside the examined biological tissue to eliminate use of the reflected photons, said computer controlled system being programmed to calculate tissue oxygenation from said detected optical data, said computer controlled system being programmed to generate an image of the examined tissue based on said calculated tissue oxygenation.

2. The optical system of claim 1 further including a fresnel lens, associated with said light detector, for collecting light emerging from the examined tissue.

3. The optical system of claim 1, wherein said light detector includes an intensified charge coupled device (ICCD).

4. The optical system of claim 1, wherein said electronics includes a time-resolved spectroscopic (TRS) system.

5. The optical system of claim 1, wherein said electronics includes a phase modulation system (PMS).

6. The optical system of claim 1, wherein said electronics includes a phased array system.

7. The optical system of claim 1, wherein said electronics includes a continuous wave (CW) system.

8. The optical system of claim 1 further including a tissue tracking system constructed to tract position of the tissue area.

9. An optical system for examination of brain tissue of a subject undergoing a security check, comprising:
   a light source for generating a light beam of a wavelength in a visible to infra-red range to be introduced in biological tissue spaced apart from said source;
   a scanning and irradiation system constructed to receive said generated light beam and irradiate a tissue area of the biological tissue to be examined by scanning said light beam, said scanning and irradiation system being spaced apart from the tissue area;
   a light detector located away from the head and constructed to detect light that has migrated in the examined biological tissue; and
   a computer controlled system including electronics for controlling said light source, said light detector and said scanning and irradiation system, said computer controlled system being constructed to eliminate after detection the reflected photons in detected optical data used for tissue examination, said computer controlled system being programmed to calculate tissue oxygenation and being programmed to generate an image of the examined tissue based on said calculated tissue oxygenation.

10. The optical system of claim 9 further including a fresnel lens associated with said light detector.

11. The optical system of claim 9, wherein said light detector includes an intensified charge coupled device (ICCD).

12. The optical system of claim 9, wherein said electronics includes a phase modulation system (PMS).

13. The optical system of claim 9, wherein said electronics includes a time-resolved spectroscopic (TRS) system.

14. The optical system of claim 9 further including a tissue tracking system constructed to tract position of the tissue area.

15. An optical method for examination of biological tissue, comprising:
   generating a light beam of a wavelength in a visible to infra-red range from a light source;
   receiving said generated light beam by a scanning and irradiation system being spaced apart from the biological tissue to be examined;
   irradiating a tissue area of the examined biological tissue by scanning said light beam over a the tissue area, said light beam propagating in air to the tissue area;
   detecting by a light detector, located away from the examined biological tissue, light that has migrated inside the examined biological tissue and has propagated in air from the examined biological tissue;
   controlling operation of said light source and said light detector;
   separating reflected photons from photons that have migrated inside the examined biological tissue by eliminating after detection the reflected photons in the detected optical data used for tissue examination;
   calculating tissue oxygenation of the examined tissue; and
   generating an image of the examined tissue based on said tissue oxygenation.

16. The method of claim 15 including evaluating said detected light to determine a brain function of the subject.

17. The method of claim 16 including providing brain stimulation while irradiating said tissue area.

18. The method of claim 17, wherein said acts of irradiating and detecting optical radiation are performed without said brain stimulation to obtain "rest" optical data, and said acts of irradiating and detecting optical radiation are performed while providing said brain stimulation to obtain "functional" optical data.

19. The method of claim 15 further including introducing and detecting optical radiation to obtain "background" optical data.

20. The method of claim 15, including tracking position of the tissue area.

21. The method of claim 15, wherein said act of detecting includes detecting fluorescent light emitted from the examined tissue.

22. An optical method for examination of brain tissue of a subject undergoing a security check, comprising:
   generating a light beam of a wavelength in a visible to infra-red range from a light source;
   receiving said generated light beam by a scanning and irradiation system being spaced apart from the biological tissue to be examined;

irradiating a tissue area of the brain tissue by scanning said light beam over the tissue area, said light beam propagating in air to the tissue area;

detecting by a light detector, located away from the examined brain tissue, light that has migrated inside the examined brain tissue and has propagated in air from the examined biological tissue;

controlling operation of said light source and said light detector;

separating reflected photons from photons that have migrated inside the examined brain tissue to prevent detection of the reflected photons by the light detector or eliminating after detection the reflected photons in the detected optical data used for tissue examination;

providing brain stimulation while irradiating said tissue area;

determining tissue oxygenation of the examined brain tissue; and providing a measure of deceit for the subject undergoing a security check based on said tissue oxygenation.

23. The method of claim 22, including tracking position of the tissue area.

24. The method of claim 23, wherein said providing said brain stimulation includes providing visual stimulation.

25. The method of claim 23, wherein said providing said brain stimulation includes stimulating cognitive function of the brain.

26. The method of claim 23, wherein providing said brain stimulation includes stimulating memories stored in the brain.

27. The method of claim 23, wherein said providing said brain stimulation includes providing auditory stimulation.

28. The method of claim 22, wherein said acts of irradiating and detecting optical radiation are performed without said brain stimulation to obtain "rest" optical data, and said acts of irradiating and detecting optical radiation are performed while providing said brain stimulation to obtain "functional" optical data.

29. The method of claim 22 further including introducing and detecting optical radiation to obtain "background" optical data.

30. The method of claim 22, wherein said act of detecting includes detecting fluorescent light emitted from the examined tissue.

* * * * *